United States Patent
Bonadio et al.

(10) Patent No.: US 11,202,653 B2
(45) Date of Patent: Dec. 21, 2021

(54) ACCESS PORT DEVICE

(71) Applicant: ATROPOS LIMITED, County Wicklow (IE)

(72) Inventors: Frank Bonadio, County Wicklow (IE); Stephen Williams, County Dublin (IE); Lucy Dolores Halpin, Dublin (IE)

(73) Assignee: ATROPOS LIMITED, County Wicklow (IE)

( * ) Notice: Subject to any disclaimer, the term of this patent is extended or adjusted under 35 U.S.C. 154(b) by 186 days.

(21) Appl. No.: 15/755,950

(22) PCT Filed: Aug. 26, 2016

(86) PCT No.: PCT/EP2016/070250
§ 371 (c)(1),
(2) Date: Feb. 27, 2018

(87) PCT Pub. No.: WO2017/036989
PCT Pub. Date: Mar. 9, 2017

(65) Prior Publication Data
US 2018/0338777 A1 Nov. 29, 2018

Related U.S. Application Data

(60) Provisional application No. 62/211,353, filed on Aug. 28, 2015, provisional application No. 62/308,286, filed on Mar. 15, 2016.

(51) Int. Cl.
*A61B 1/32* (2006.01)
*A61B 17/34* (2006.01)
(Continued)

(52) U.S. Cl.
CPC ...... *A61B 17/3423* (2013.01); *A61B 17/0293* (2013.01); *A61B 17/3421* (2013.01);
(Continued)

(58) Field of Classification Search
CPC combination set(s) only.
See application file for complete search history.

(56) References Cited

U.S. PATENT DOCUMENTS

| 6,254,534 B1 | 7/2001 | Butler et al. | |
| 6,846,287 B2 * | 1/2005 | Bonadio | A61B 17/0293 |
| | | | 128/846 |

(Continued)

FOREIGN PATENT DOCUMENTS

EP    2226026 A1    9/2010

OTHER PUBLICATIONS

International Search Report dated Dec. 22, 2016, in International Application No. PCT/EP2016/070250 (6 pages).

*Primary Examiner* — Sameh R Boles
(74) *Attorney, Agent, or Firm* — Bookoff McAndrews, PLLC

(57) ABSTRACT

A valve component (1) of the invention comprises a main valve (2) which is located on a centre line and at least one auxiliary valve (3) which is located radially outwardly of the main valve (2). The main valve may be used for sealing engagement with a cannula. In some cases the cannula may be used for introduction of a number of robotically controlled surgical instruments generally, including a camera. The auxiliary valves (3) may be utilised to introduce another instrument through the valve component. The valve component is mounted in a manner which ensures that the valve component (1) is rotatable about a centre line through the axis of the valve component (1). This ensures that the valve component (1) can be rotated relative to a cannula inserted through the main valve (2) and consequently that the auxiliary valves (3) are rotatable relative to the cannula allowing the auxiliary valves (3) to be positioned to facilitate opti- (Continued)

mum access and manipulation for an auxiliary instrument(s) inserted through the auxiliary valve(s) (2).

20 Claims, 28 Drawing Sheets

(51) Int. Cl.
*A61B 17/02* (2006.01)
*A61B 34/30* (2016.01)
(52) U.S. Cl.
CPC ...... *A61B 17/3462* (2013.01); *A61B 17/3431* (2013.01); *A61B 34/30* (2016.02); *A61B 2017/3445* (2013.01); *A61B 2017/3449* (2013.01); *A61B 2017/3466* (2013.01)

(56) References Cited

U.S. PATENT DOCUMENTS

| | | |
|---|---|---|
| 7,559,893 B2 | 7/2009 | Bonadio et al. |
| 2005/0090717 A1 | 4/2005 | Bonadio et al. |
| 2010/0217081 A1 | 8/2010 | Bonadio et al. |
| 2010/0312063 A1* | 12/2010 | Hess ............... A61B 17/3423 600/204 |
| 2014/0275796 A1 | 9/2014 | McGrogan et al. |

* cited by examiner

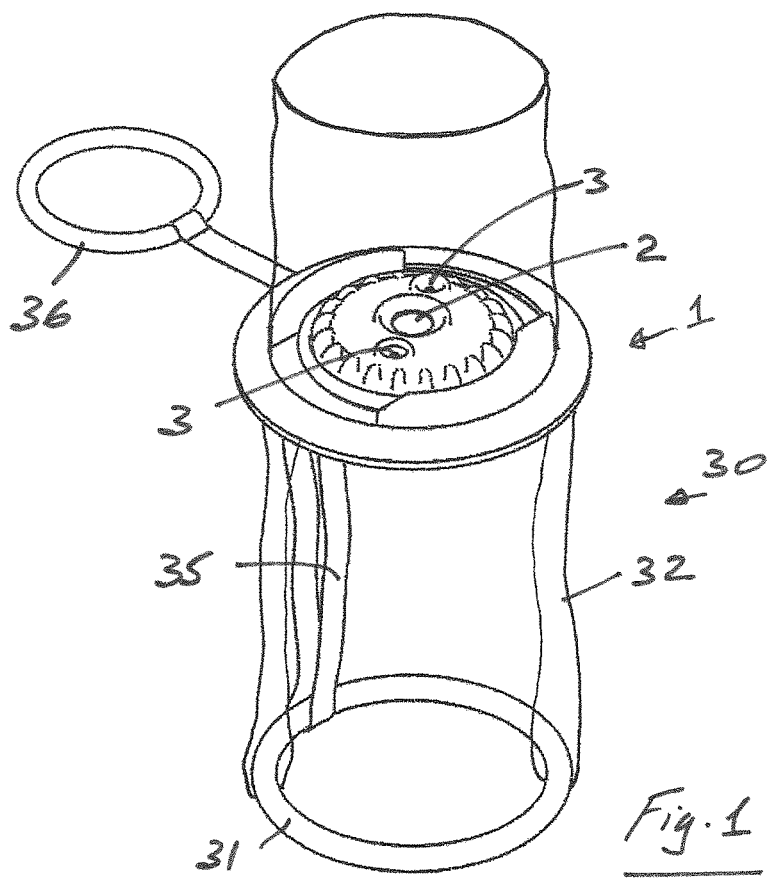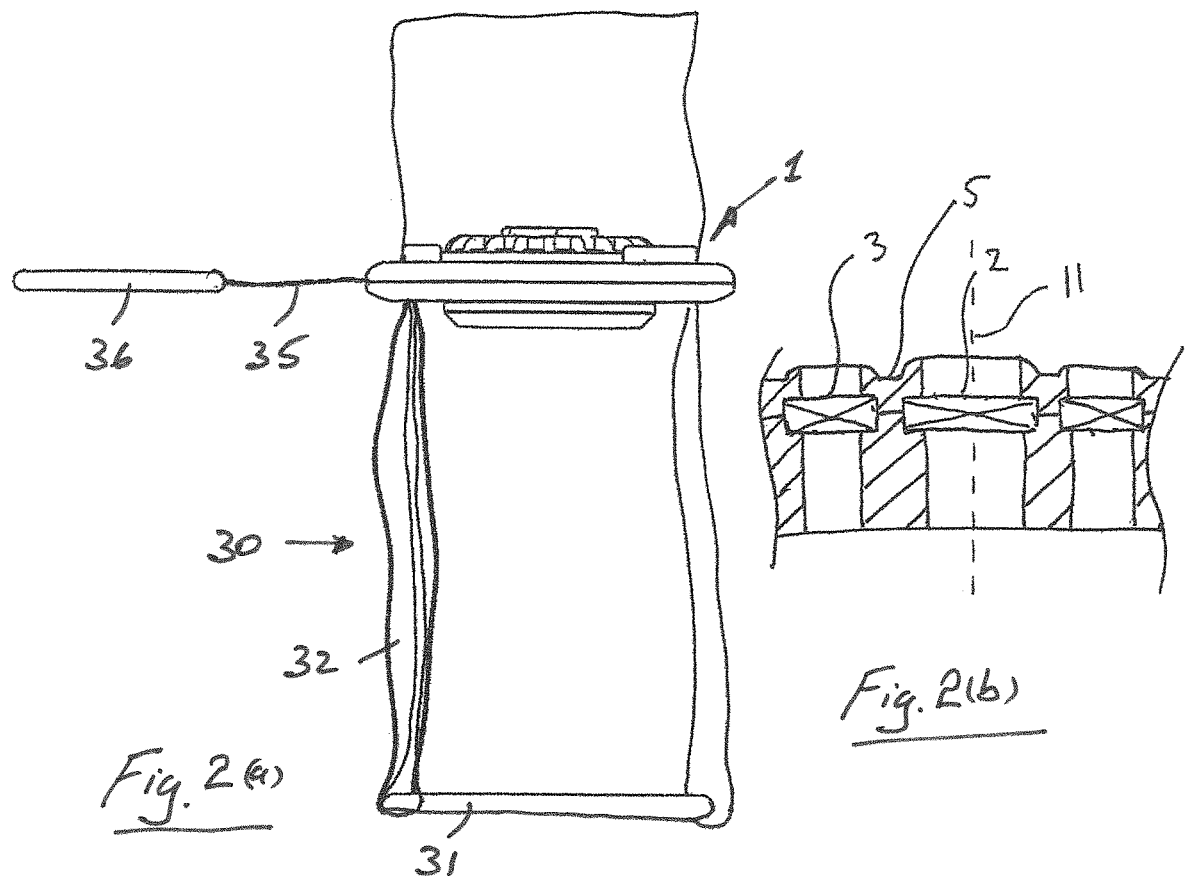

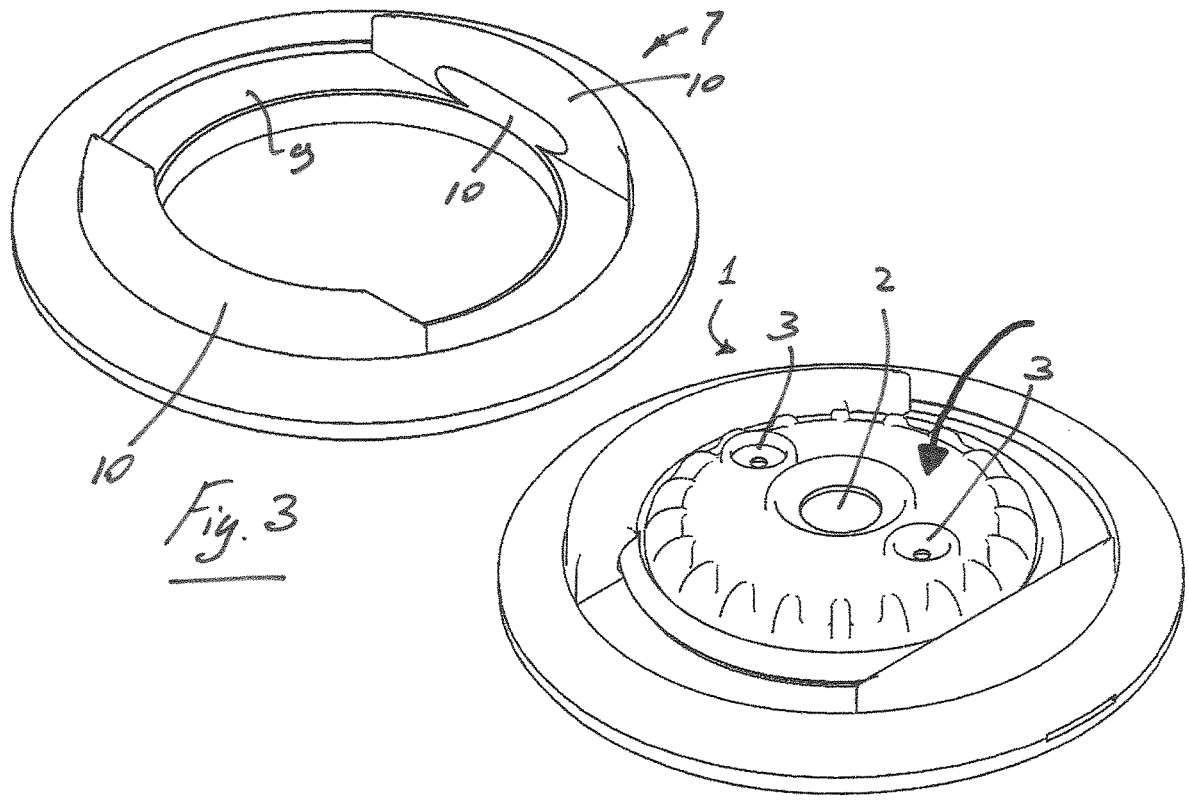
Fig. 3
Fig. 4
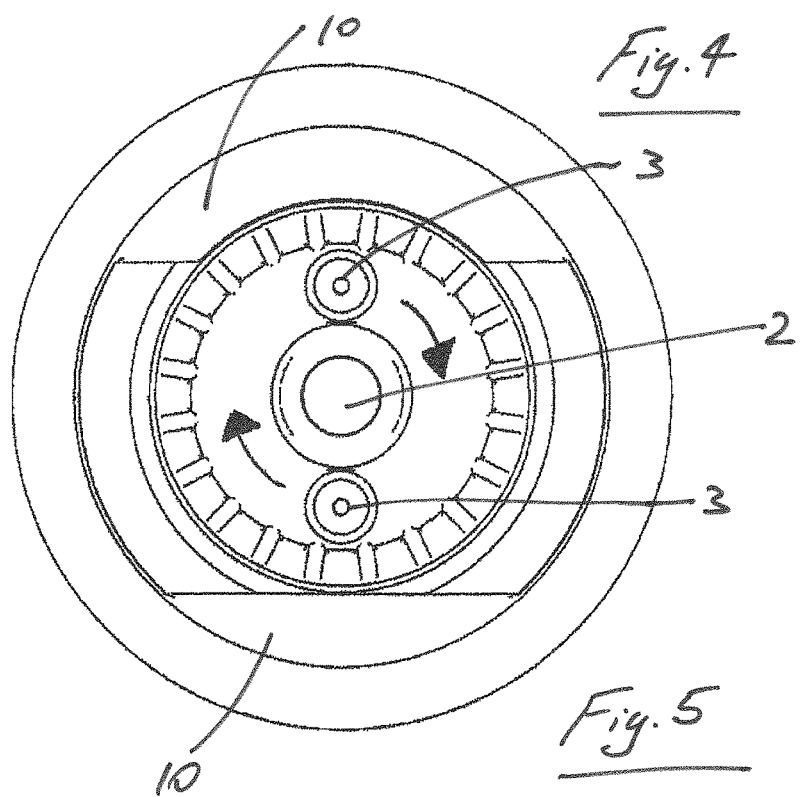
Fig. 5

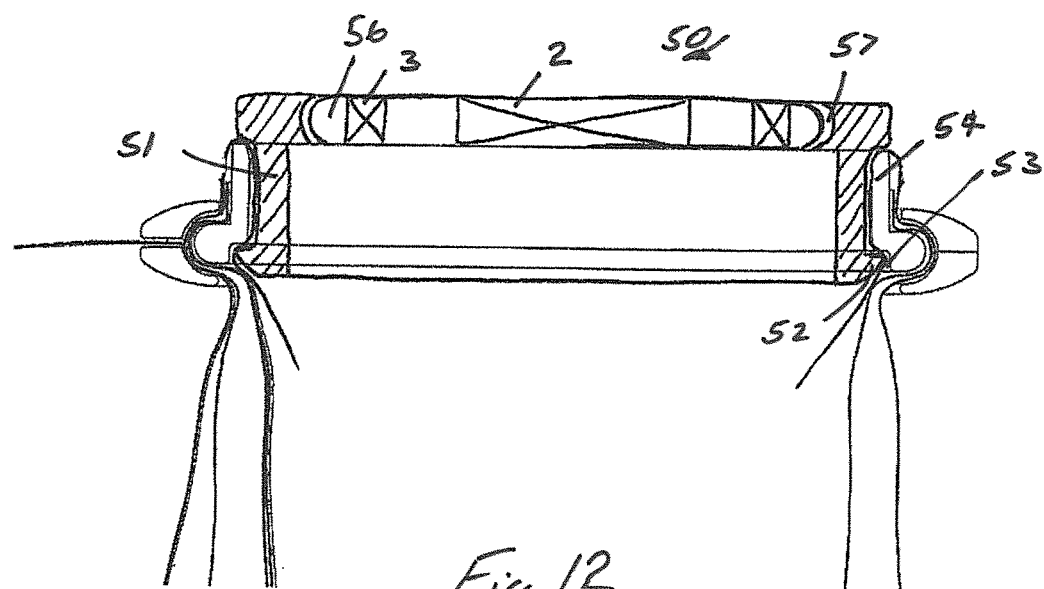
Fig. 12
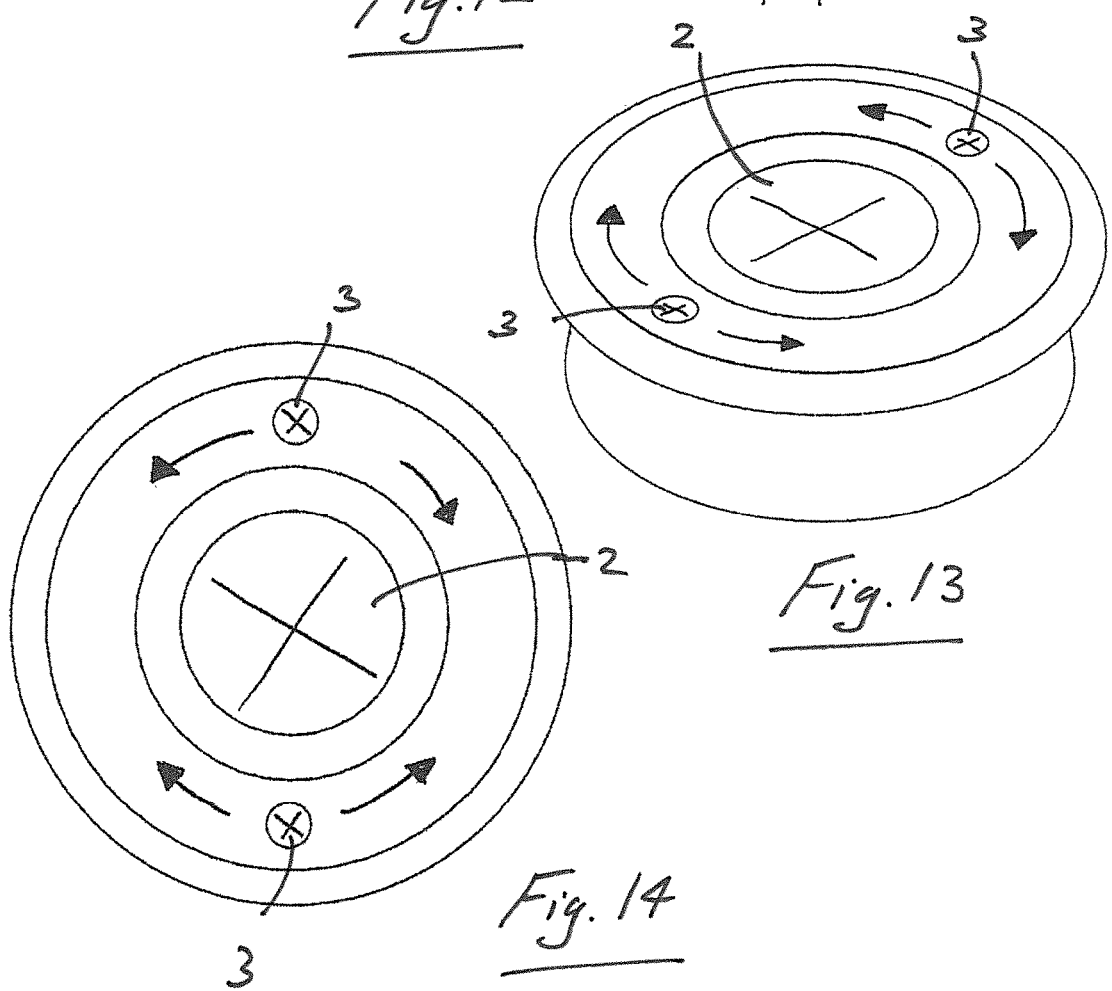
Fig. 13
Fig. 14

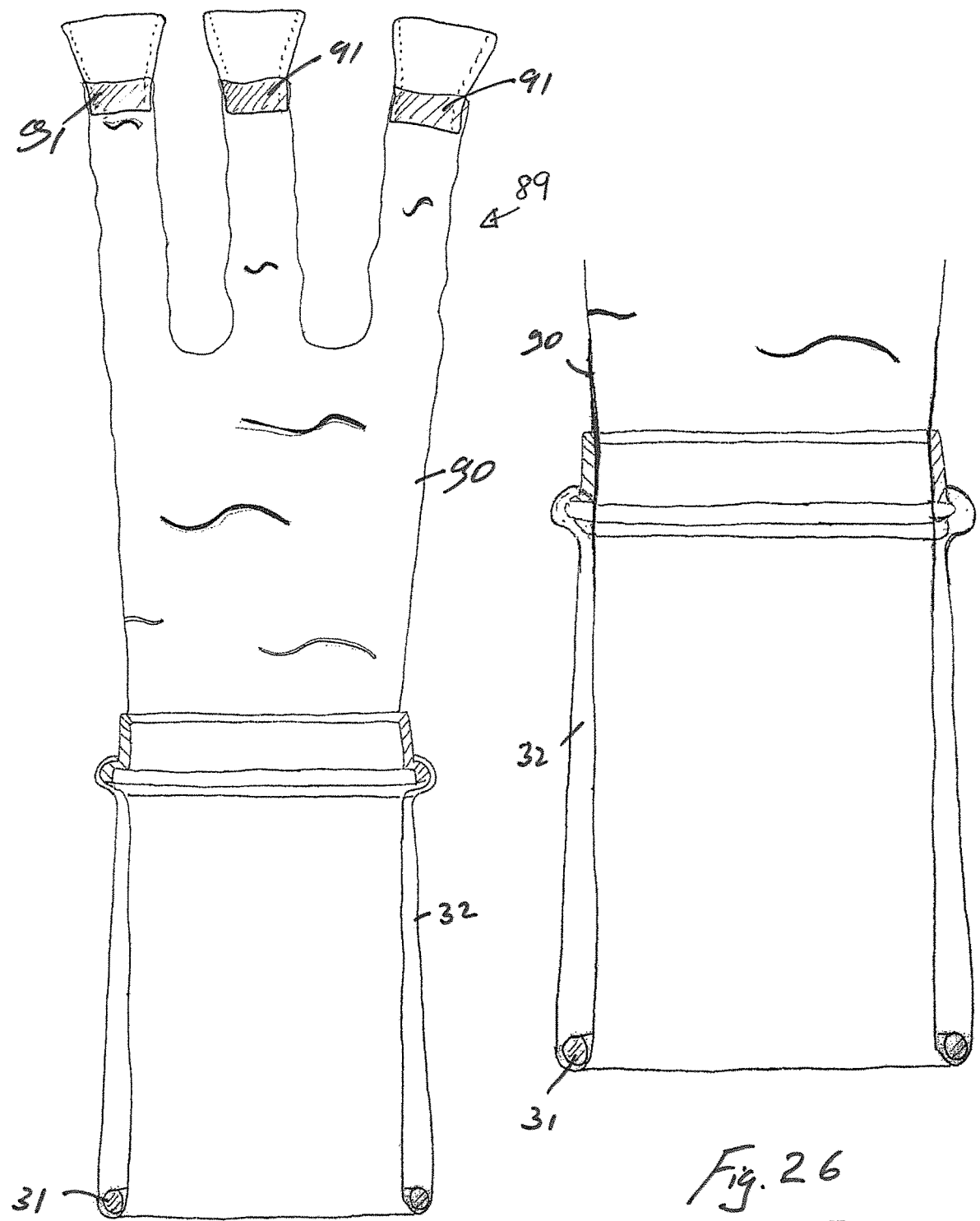

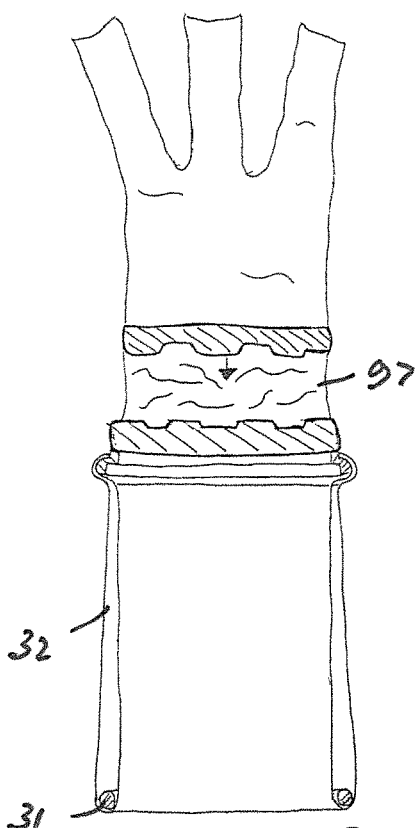
Fig. 27
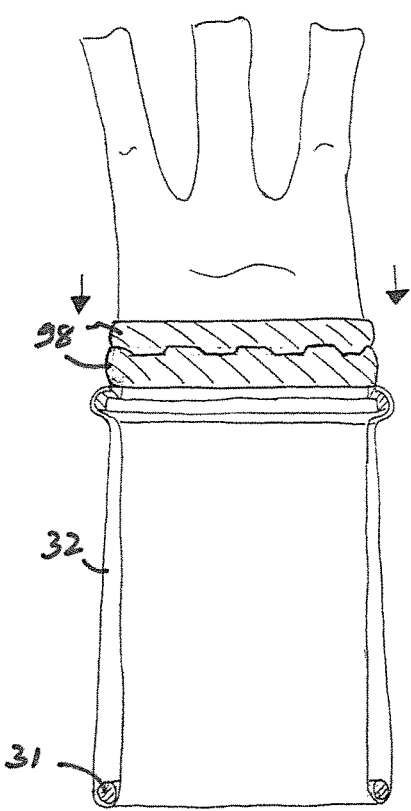
Fig. 28
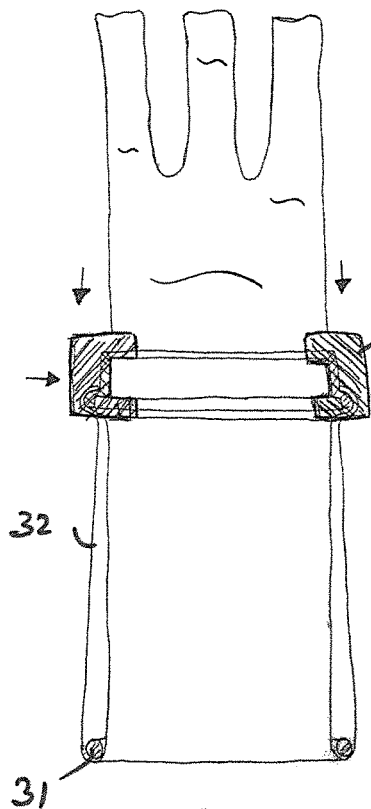
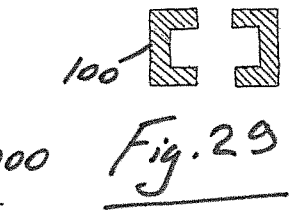
Fig. 29
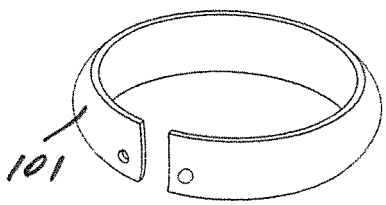
Fig. 31
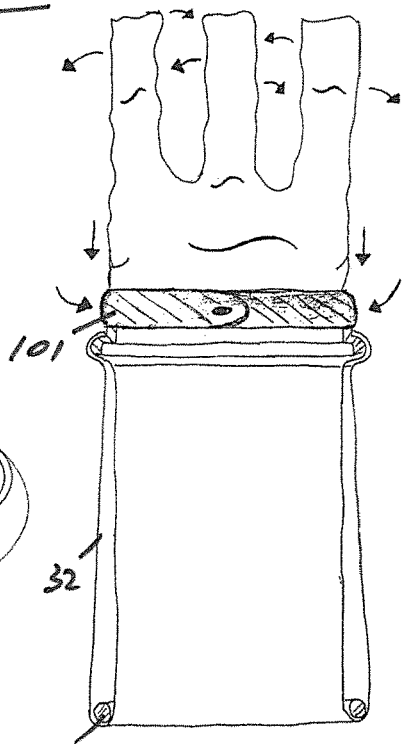
Fig. 30
Fig. 32

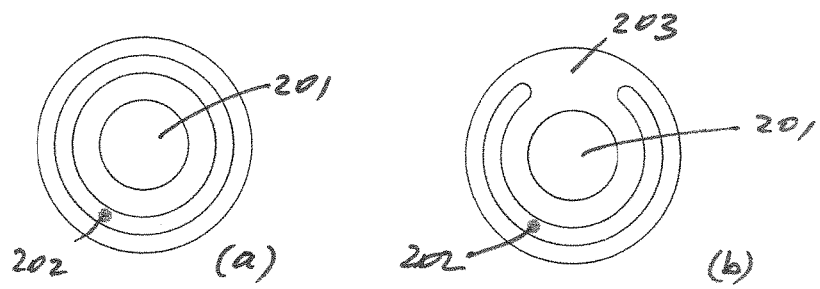
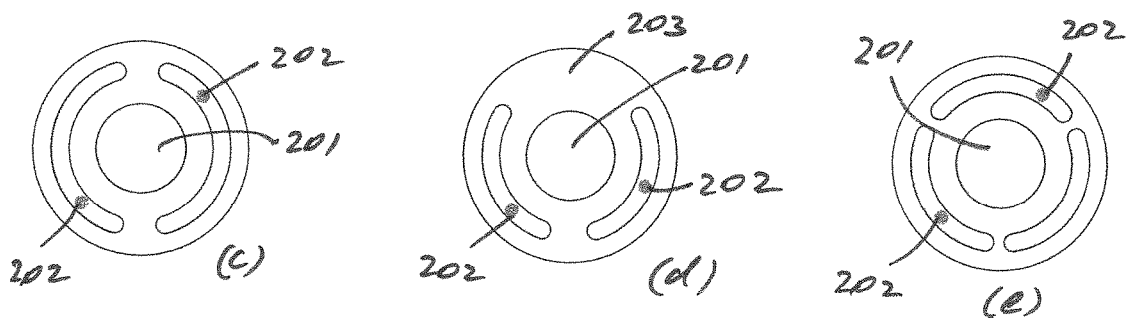
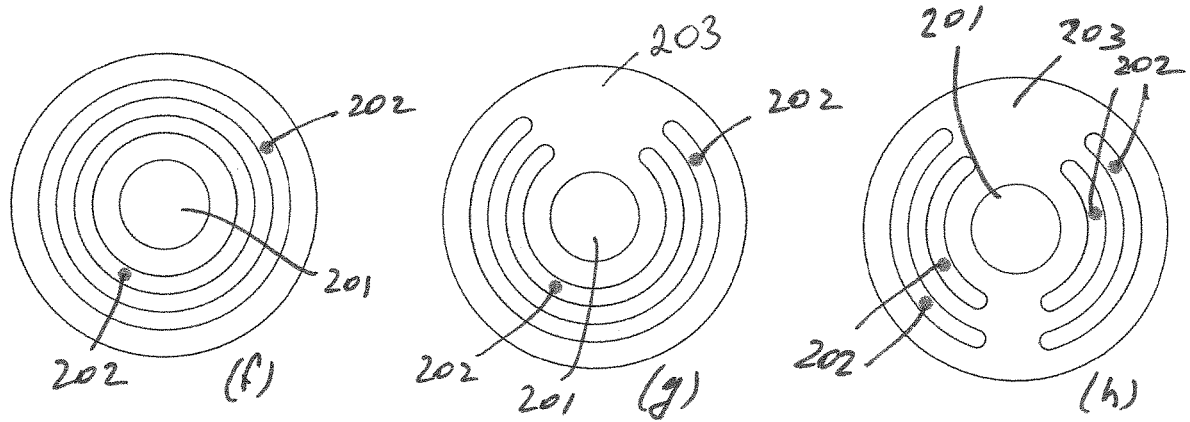
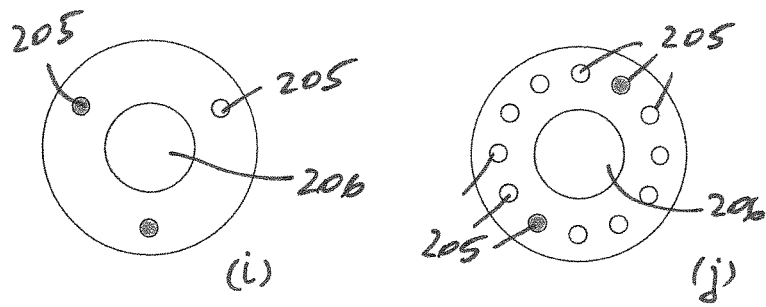
Fig. 33

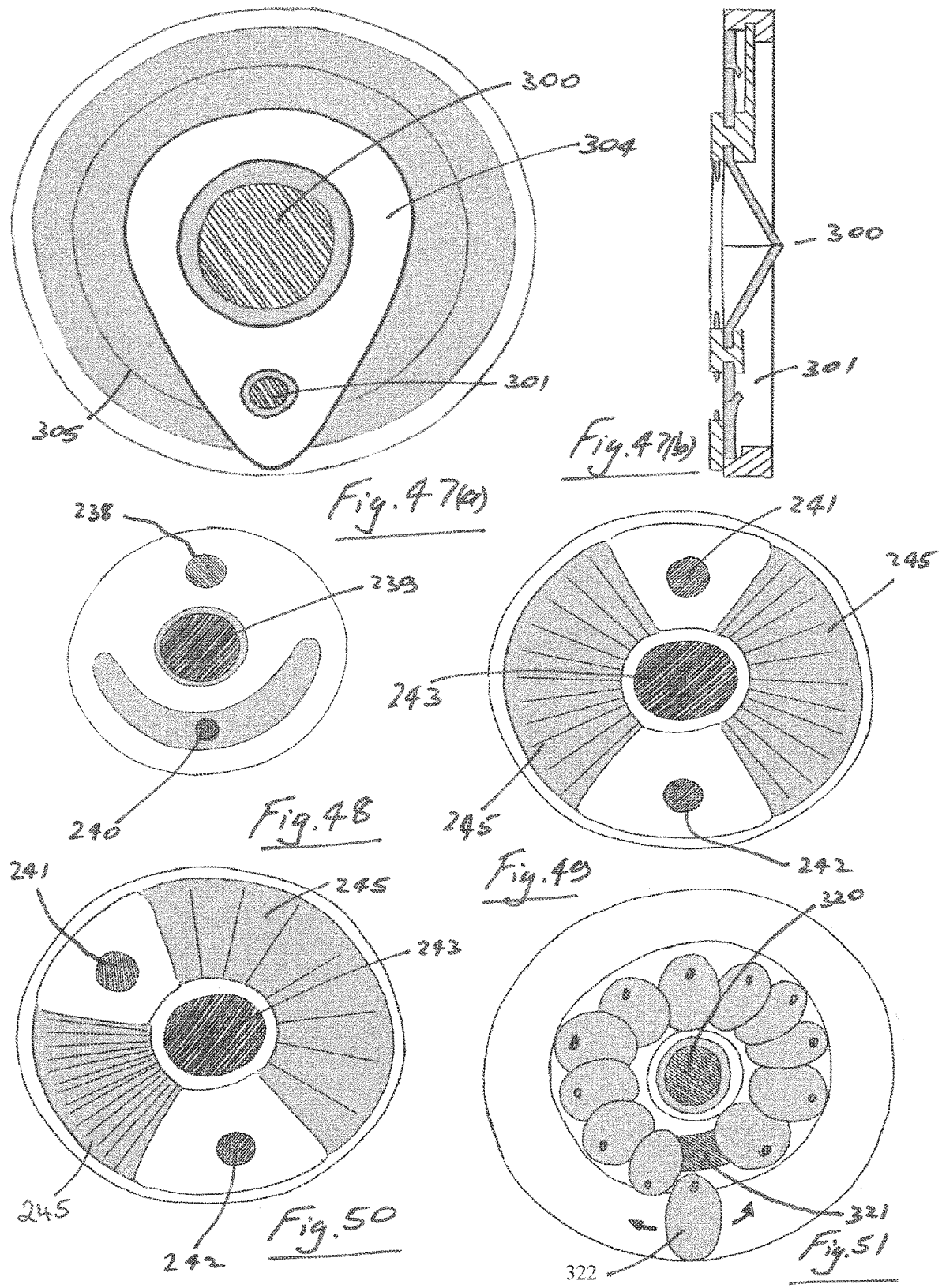

ACCESS PORT DEVICE

CROSS-REFERENCE TO RELATED APPLICATIONS

This application is the U.S. national phase entry under 35 U.S.C. § 371 of International Application No. PCT/EP2016/070250, filed on Aug. 26, 2016, which claims priority to U.S. Provisional Application No. 62/211,353, filed on Aug. 28, 2015, and U.S. Provisional Application No. 62/308,286, filed on Mar. 15, 2016, the entireties of which are herein incorporated by reference.

INTRODUCTION

This invention relates to an access port device, especially for use in robotic surgery.

Minimally invasive surgery involves a patient being operated on through a small incision (generally through the abdomen) or through a natural body orifice. We have developed various devices for retracting the incision or opening to enlarge the access area such as those described in U.S. Pat. Nos. 6,254,534, 6,846,287 and 7,559,893.

Instruments are inserted into the operative area through the incision or orifice. In some instances at least one additional instrument is inserted through a separate cannula. The instruments may be manipulated manually or using a robot.

There is a need for an access device which will facilitate enhanced movement of instruments within the operative field to provide enhanced efficiency of operation.

STATEMENTS OF INVENTION

Described is a valve component for an instrument access device, the valve component being adapted for or configured to be mounted to an access port device. The valve component has a main valve which is located on a center line of the valve component and at least one auxiliary valve which is located radially outwardly of the main valve.

According to the invention there is provided an instrument access device comprising:— a base;

a valve component which is rotatably mounted to the base;

the valve component having a main valve which is located on a center line of the valve component and at least one auxiliary valve which is located radially outwardly of the main valve.

In one embodiment the base comprises portion of a wound retractor.

In one case the wound retractor includes a longitudinal axis;

a proximal ring-shaped portion for location externally of a wound interior;

a distal ring-shaped portion for location within a wound interior; and a retraction portion extending proximally from the distal ring-shaped portion and laterally movable with respect to the proximal ring-shaped portion.

In one embodiment the base includes the proximal ring-shaped portion of the retractor and the valve component is rotatably mounted to the proximal ring-shaped portion.

The proximal ring-shaped portion may comprise an outer proximal ring and an inner proximal ring.

In one embodiment the valve component is mounted to the inner proximal ring. The valve component may be rotatably mounted to the inner proximal ring.

In another embodiment the valve component is non-rotatably mounted to the inner proximal ring and the inner proximal ring is rotatably mounted to the outer proximal ring.

In one case the valve component comprises at least two auxiliary valves.

A first auxiliary valve may be movable independently of a second auxiliary valve.

In one embodiment the valve component comprises a first valve platform for a first auxiliary valve and a second valve platform for a second auxiliary valve. The first valve platform may be movable relative to the second valve platform. The first valve platform may be rotatable relative to the second valve platform.

In one embodiment the instrument access device comprises a seal between the valve component and the base. The seal may comprise a rotary lip seal.

In one embodiment the valve component is releasably mounted to the base. The instrument access device may comprise a retainer for retaining the valve component mounted to the base.

In one embodiment the instrument access device comprises a connector portion configured to releasably mount the valve component to the base. The connector portion may include a radially outer protruding member configured to engage with a radially inner part of the base.

The distal ring-shaped portion may include an O-ring.

The retraction portion may include a retracting sleeve. In one case the retracting sleeve extends in two layers between the distal ring-shaped portion and the proximal ring-shaped portion.

In one embodiment a proximal portion of the retracting sleeve is split to facilitate folding of the sleeve away from the field of the valve component. The instrument access device may comprise a clamping device for mounting the distal split ends of the sleeve to the distal ring-shaped portion.

The invention also provides an instrument access device comprising a central access port and at least one auxiliary access port which is offset from the central access port.

In one embodiment the instrument access device comprises a plurality of auxiliary access ports which are spaced-apart around the central port. In one case at least one of the auxiliary access ports is rotatable with respect to the central access port. The or each rotatable auxiliary port may be rotatable through an angle such as an angle of at least 60°, at least 90°, at least 120°, at least 150°, at least 180°, at least 210°, at least 240°, at least 270°, at least 300°, at least 330°, with respect to the central port.

In one embodiment there are at least two rotatable auxiliary ports which are rotatable in the same orbit around the central port.

In another embodiment there are at least two rotatable auxiliary ports which are rotatable in different orbits around the central port.

The instrument access device preferably comprises a central seal for sealing with an instrument inserted through the central port.

The instrument access device preferably comprises an auxiliary seal for sealing with an instrument inserted through the auxiliary port.

The auxiliary seal is preferably configured to facilitate rotation around the central port.

The auxiliary seal may be of a flexible material or a self-sealing material such as a gel.

In one case a separate auxiliary seal is provided for each auxiliary port.

In another case at least some of the auxiliary ports share a common auxiliary seal.

In one embodiment the auxiliary seal comprises at least two circumferentially extending sealing members which are overlapped at a circumferential joint therebetween to maintain substantial sealing with an auxiliary instrument inserted through the joint.

In one aspect the instrument access device comprises a cap at least partially overlying the joint. The cap may be rotatable.

The instrument access device may comprise a number of access port elements that are rotatable with respect to one another and a seal between the rotatable access port elements.

In some cases the seal comprises an O-ring or skirt-type seal. The seal may be a dynamic seal, for example, the seal may be inflatable such as by using a supply of insufflation gas.

In some cases the seal comprises a first component associated with one access port element and a second component associated with another access port element. The first and second seal components are optionally overlapped and/or interengagable.

The seal may be configured to increase sealing in response to insufflation.

In one embodiment the valve component comprises a housing for supporting the valves.

The valves may be adapted to receive surgical instruments.

In some cases the main valve has a lateral dimension, transverse to said centre line, which is greater than the lateral dimension of the auxiliary valve.

In one embodiment the main valve is adapted to receive a cannula which may be sized to receive at least one instrument which is adapted to be robotically controlled.

In some embodiments the cannula is sized to receive a plurality of robotically controlled instruments. At least one of the robotically controlled instruments may comprise a camera.

The invention also provides an instrument access device comprising:— a wound retractor including:
a longitudinal axis;
a proximal base for location externally of a wound interior;
a distal ring for location within a wound interior; and
a retraction sleeve extending between the proximal base and the distal ring, the retraction sleeve being adjustable to shorten the extent of the sleeve between proximal base and the distal ring; and
a valve component rotatably coupled to the proximal base, the valve component including:
a first valve centered about a center line of the valve component, and
at least one second valve located radially outwardly of the first valve.

The proximal base may include an inner ring and an outer ring, and the retraction sleeve extends between the inner and outer ring. The valve component may be rotatably coupled to the inner ring, and the inner ring is fixedly coupled to the other ring. In one case the retraction sleeve extends in two layers between the proximal base and the distal ring.

The invention further provides an instrument access device comprising:— a wound retractor including a proximal base for location externally of a wound interior; and
a valve component rotatably coupled to the proximal base, the valve component including:
one of a radial protrusion or a radial groove sized to mate with one of a radial protrusion or a radial groove of the proximal base, the mating connection allowing for coupling, uncoupling, and rotation of the valve component relative to the proximal base;
a first valve centered about a center line of the valve component, and
at least one second valve located radially outwardly of the first valve.

In one embodiment the wound retractor further includes:
a distal ring for location within a wound interior; and
a retraction sleeve extending between the proximal base and the distal ring, the retraction sleeve being adjustable to shorten the extent of the sleeve between proximal base and the distal ring, and the mating connection is separate from the retraction sleeve so that coupling or uncoupling of the valve component from the proximal base does not move the extent of the sleeve between proximal base and the distal ring.

In one case a surface of the radial protrusion is circumferentially slidable against a surface of the radial groove to facilitate rotation of the valve component relative to the proximal base.

The invention also provides an instrument access device comprising:— a wound retractor having a longitudinal axis and including a proximal base for location externally of a wound interior; and
a valve component rotatably coupled to the proximal base, the valve component including:
a first valve centered about a center line of the valve component, and
at least one second valve located radially outwardly of the first valve, the first and second valve lying in a common plane, the common plane extending normal to the longitudinal axis.

In one case the first and second valves are located in a proximally-open recess of the valve component.

In one case the first and second valves are located between proximal and distal portions of the valve component.

In one case the first and second valves are at a proximal end of the valve component.

In one case the first and second valves are recessed from a proximal end of the valve component.

The invention further provides an instrument access device comprising:— a wound retractor including a proximal base for location externally of a wound interior; and
a valve component coupled to the proximal base, the valve component including:
an outer ring member rotatably coupled to the proximal base and including an outer valve; and
an inner ring member rotatably coupled to the outer ring and including an inner valve centered about a center line of the valve component.

In one embodiment the inner ring includes an additional inner valve located radially outwardly of the inner valve.

In one case the inner ring member and the outer ring member are slidingly and sealingly engaged at an interface between the inner ring member and the outer ring member. The interface may include a protrusion on one of the inner ring member and the outer ring member, received in a groove on the other of the inner ring member and the outer ring member.

In one case the interface includes a lip seal on one of the inner ring member and the outer ring member, for engaging a surface of the other of the inner ring member and the outer ring member.

BRIEF DESCRIPTION OF THE DRAWINGS

The invention will be more clearly understood from the following description of an embodiment thereof, given by way of example only, with reference to the accompanying drawings, in which:

FIG. 1 is an isometric view of an access port device according to the invention;

FIGS. 2(a) and 2(b) are a side view of and a partial cross-sectional view through, respectively, the port device of FIG. 1;

FIG. 3 is an isometric view of a proximal ring assembly;

FIG. 4 is a view of the proximal ring assembly of FIG. 3 with a valve unit in situ;

FIG. 5 is a plan view of the valve unit in situ within the proximal ring assembly;

FIGS. 12 to 14 are a series of images of a further access port device;

FIGS. 25 and 26 are views of a further access port device;

FIGS. 27 to 32 are a series of images of further access port devices of the invention;

FIG. 33(a) to (j) are a series of images illustrating different assistant port configurations around a large central port;

FIGS. 47 to 51 are views of further access ports of the invention;

DETAILED DESCRIPTION

A valve component 1 of the invention comprises a main valve 2 which is located on a centre line of the valve component 1, for example centred about the centre line of the valve component 1, and at least one auxiliary valve 3 which is located radially outwardly of the main valve 2. One or more of the main valve 2 and the at least one auxiliary valve 3 may include a gel seal, a lip seal, and/or any other suitable seal for sealing engaging an outer surface of an instrument inserted through the valve(s).

The main valve may, for example, be used for sealing engagement with a cannula. In some cases the cannula may be used for introduction of a number of robotically controlled surgical instruments generally, including a camera.

The auxiliary valve 3 may be utilised to introduce another instrument through the valve component.

Typically the main valve 2 has a diameter of about 25 mm and the auxiliary valve 3 has a diameter of 5 mm. There may be two auxiliary valves 3 which may be arranged in any suitable configuration, for example, opposed on a diameter extending through a centre line of the main valve 2.

The valve component is mounted in a manner which ensures that the valve component 1 is rotatable about a centre line through the axis of the valve component 1. This ensures that the valve component 1 can be rotated relative to a cannula inserted through the main valve 2 and consequently that the auxiliary valves 3 are rotatable relative to the cannula allowing the auxiliary valves 3 to be positioned to facilitate optimum access and manipulation for an auxiliary instrument(s) inserted through the auxiliary valve(s) 2.

Figures 15A, 15B, 15C:
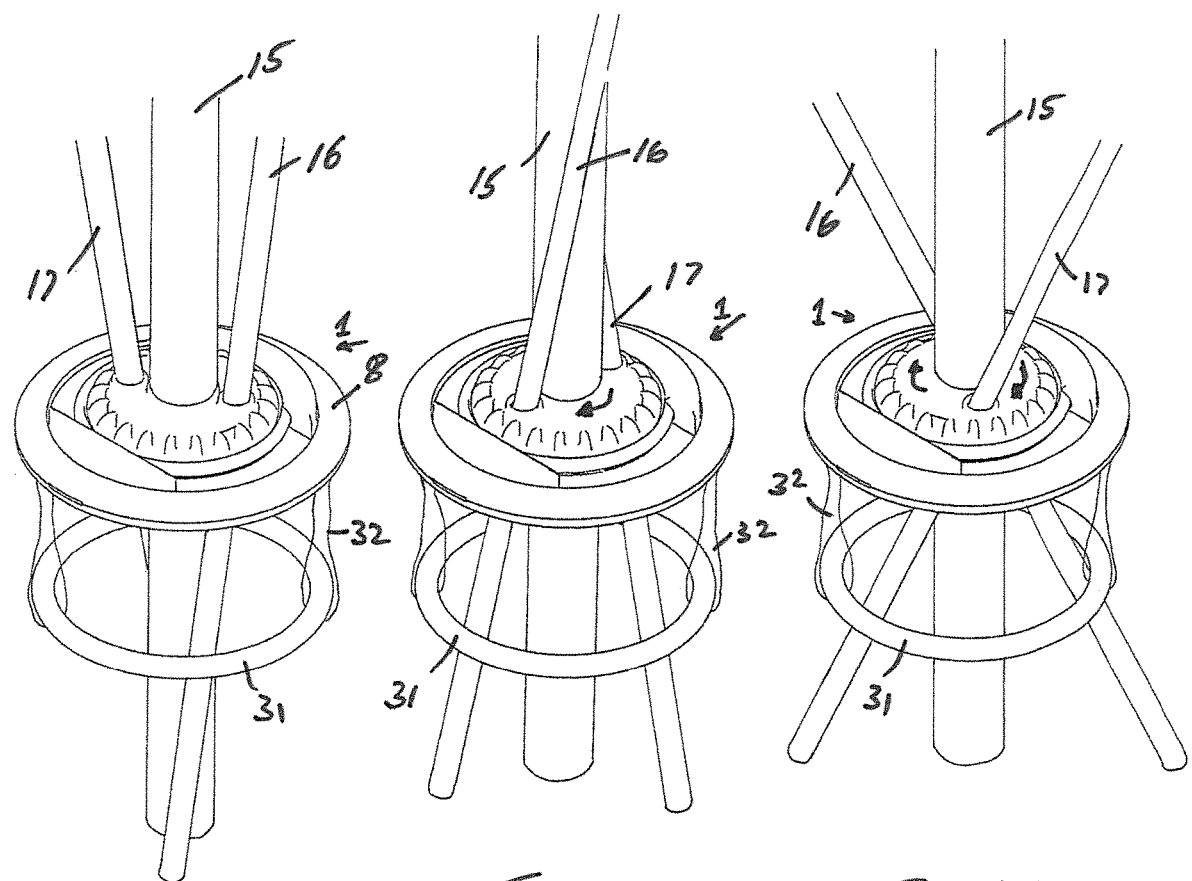
FIGS. 15(a) to 15(c) are a series of diagrams of the access port device in use with instruments in situ.

FIGS. 15(a) to 15(c) illustrate a valve component of the invention with instruments 15, 16, 17 in situ. The valve component facilitates free rotation of auxiliary or assistant valves 3 about a central valve 2 in which a larger instrument 15 such as a robotic instrument is positioned. The central instrument 15 is not impeded by the rotation of the auxiliary valves 3 around the central valve 2.

It will be appreciated that instruments inserted through the auxiliary valves may be operated manually, or robotically from a location remote from the valve unit.

The valve component 1 may be rotatably mounted to any suitable mounting component. One such mounting component is illustrated in FIGS. 3 to 5. In this case the mounting component comprises a proximal ring assembly 7 which includes an outer proximal ring 8 and an inner proximal ring 9 which is engaged with the outer proximal ring 8.

The mounting component may have any suitable mounting features to accommodate the valve component 1. For example, the mounting features may comprise receivers 10 in which the valve component may be mounted. In one instance the valve component 1 may be substantially fixedly mounted to the inner proximal ring 9 and the inner proximal ring 9 is rotatable relative to the outer proximal ring 8. In another configuration the valve component 1 is rotatably mounted to the inner proximal ring 9.

FIGS. 3 to 5 illustrates the proximal ring assembly 7 which comprises an outer proximal ring 8 and an inner proximal ring 9 (which is rotatable) within the outer proximal ring 8. The inner proximal ring 9 has mounting features such as receivers 10 for retaining the valve component as illustrated in FIG. 4. FIG. 5 illustrates the rotation of the valve component 1 within the inner proximal ring 9. Instead of having a single ring-like receiver that extends the entire way around the proximal ring 9 to hold the valve component 1, each of the receivers 10 may extend around only a portion of the proximal ring 9, thereby limiting surface contact (and frictional engagement) with the valve component 1. Limiting the contact in this way may facilitate rotation of the valve component 1 relative to the proximal ring 9 and the receivers 10 because there is less friction to impede the rotation. Alternatively, a single ring-like receiver may be used to enhance frictional engagement to, for example, help maintain relative positioning of the valve component relative to the proximal ring 9 when set.

In the embodiment of FIGS. 1 to 5 the valve component 1 is freely rotatable within the inner proximal ring 9. The valve component 1 is rotatable around a large instrument inserted through the main valve 2 and the auxiliary valves 3 (assistant port) move together as illustrated, for example, in FIGS. 15(*a*) to 15(*c*).

As shown in FIGS. 1 to 5, the main valve 2 and the auxiliary valves 3 may each be supported in a housing 5 of the valve component 1. For example, one or more of the main valve 2 and the auxiliary valve 3 may be clamped or otherwise secured between a proximal half or portion of the housing 5 and a distal half or portion of the housing 5. As shown in FIG. 2(*b*), two or more of the main valve 2 and the auxiliary valves 3 may be similarly situated, in terms of their positioning in a proximal-distal direction, along a central longitudinal axis 11 of the valve component 1. For example, at least two of the main valve 2 and the auxiliary valves 3 may lie in a common plane, the common plane extending normal to the central longitudinal axis of the valve component 1. Additionally or alternatively, the main valve 2 and/or the auxiliary valves 3 may be recessed, in that a proximal end of one or more of the main valve 2 and the auxiliary valves 3 may be recessed from a proximal end of the housing 5. The main valve 2 and the auxiliary valves 3 may pose less of an impediment to the movements of instruments inserted therein due to this low-profile configuration.

Figure 6A:
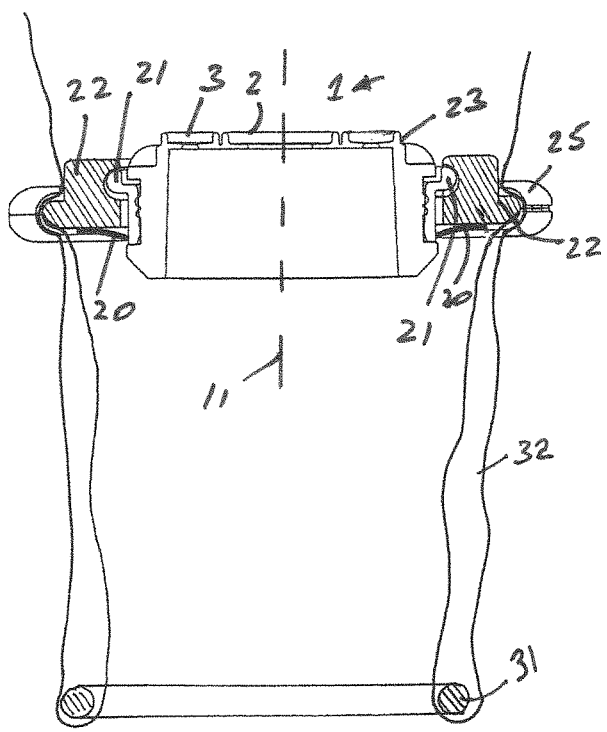
FIGS. 6(a) and 6(b) are a side, partially cross sectional view, and a close-up, partially cross sectional view, respectively, of an access port device with a double sleeve wound protector/retractor.
Figure 6B:
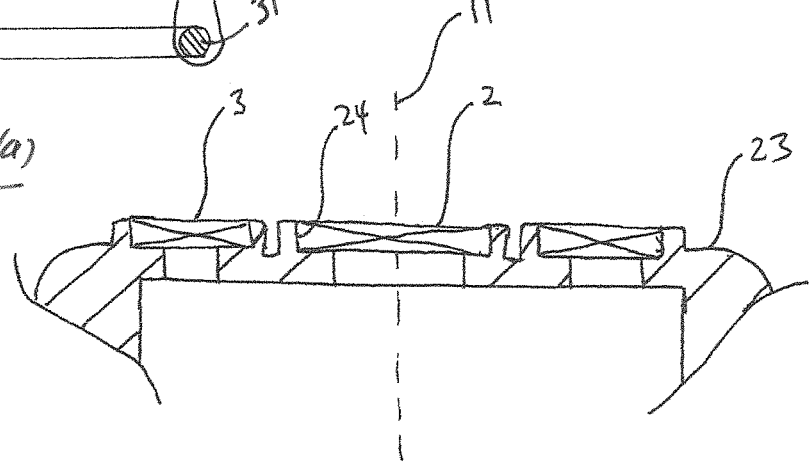

Referring to FIGS. 6(*a*), 6(*b*), and 7, in this case a valve component 1 is engaged in an inner proximal ring 21 and both the valve component 1 and the inner proximal ring 21 are rotatable within an outer proximal ring 22.

In some cases a seal such as a lip seal 20 is provided between relatively rotatable components, as shown in FIGS. 6-9. For example, one or more lip seals 20 may be provided between the inner and outer proximal rings 8, 9 or 21, 22. The one or more lip seals may extend from the outer proximal ring 8 to the inner proximal ring 9 and/or vice-versa. A similar arrangement may be provided for the proximal rings 21 and 22. Additionally or alternatively, it is contemplated that relatively rotatable components may have complementary engaging surfaces (e.g., one or more protrusions for receipt in one or more grooves or recesses) to provide sealing and sliding engagement between the components.

The valve component 1 of the invention may be mounted to a retractor 30. One such retractor 30 comprises a distal anchoring ring 31 for location within a wound interior, a retractor portion, such as a sleeve 32, and a proximal ring-shaped portion for location externally of a wound interior. The retraction portion 32 extends proximally from the distal ring 31 and is laterally movable with respect to the proximal ring-shaped portion. The proximal ring shaped portion may comprise the inner and outer proximal rings 8, 9 or 21, 22.

It will be noted that in FIGS. 6(*a*), 6(*b*), and 7 the retractor sleeve 32 is located between the proximal ring 22 and a further outer ring 25. This ensures that the sleeve 32 does not rotate when the valve component 1 is rotated. This ensures that retraction and wound protection are optimised, in use.

FIGS. 6(*a*) and 6(*b*) shows a retractor/protector comprising a double sleeve 32. One such device is described, for example, in our U.S. Pat. Nos. 6,846,287 and 7,559,893, the entire contents of both of which are incorporated herein by reference. For example, a fixed end of the sleeve 32 may be fixedly coupled to the outer proximal ring 22, while a free end of the sleeve 32 may extend between the outer proximal ring 22 and the outer ring 25.

Figure 7:
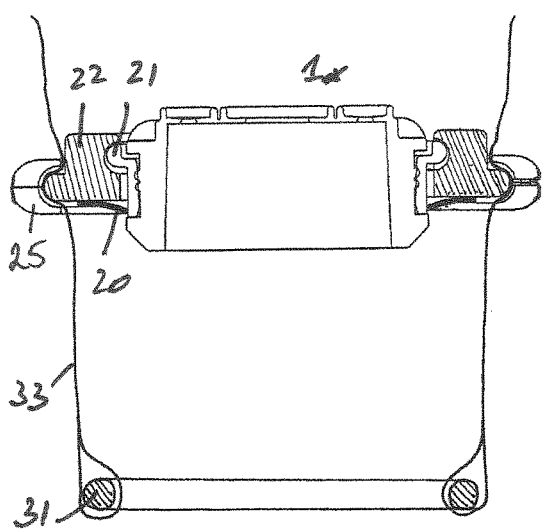
FIG. 7 is side, partially cross sectional view of a further access port device with a single sleeve wound protector/retractor.
Figure 8:
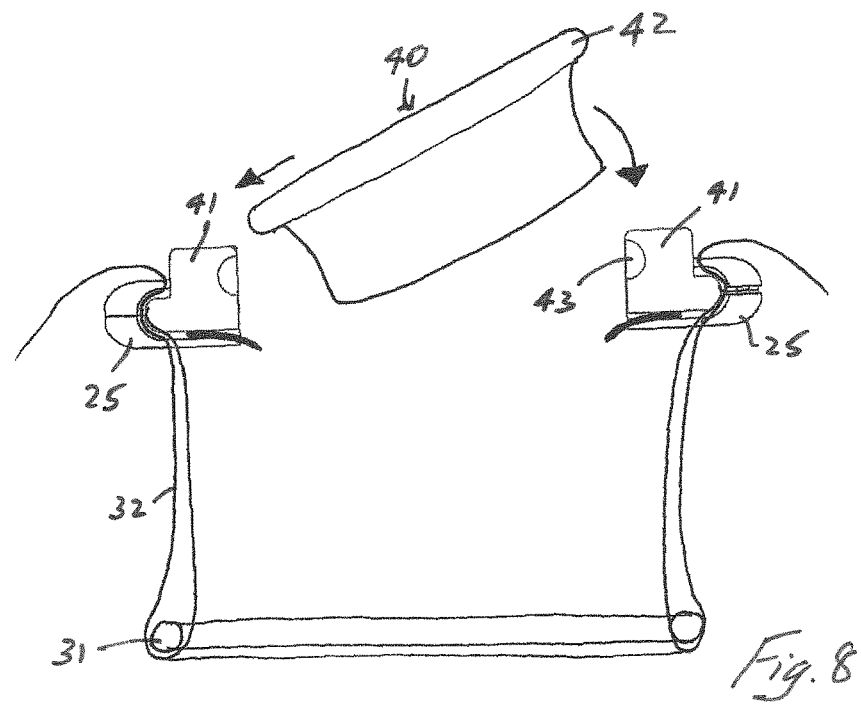
FIGS. 8 to 11 are a series of images of another access port device.
Figure 9:
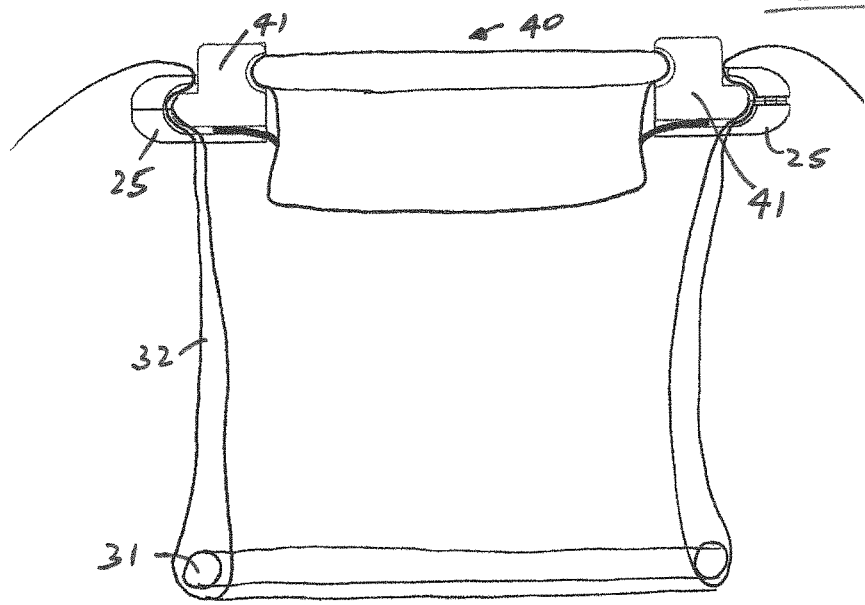
Figure 10:
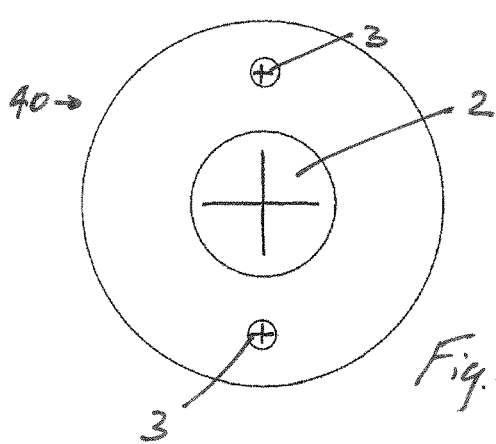
Figure 11:
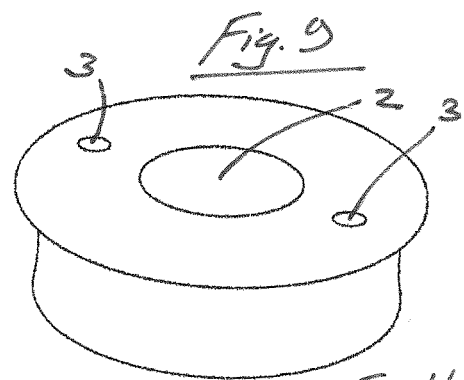

FIG. 7 shows retractor/protector comprising a single sleeve 33. One such device is described in our U.S. Pat. No. 6,254,534, the entire contents of which are incorporated herein by reference. For example, a free end of the sleeve 32 may extend between the outer proximal ring 22 and the outer ring 25.

As shown in FIGS. 6(*a*), 6(*b*), and 7, the main valve 2 and the auxiliary valves 3 may each be supported in a housing 23 of the valve component 1. Two or more of the main valve 2 and the auxiliary valves 3 may be similarly situated, in terms of their positioning in a proximal-distal direction, along a central longitudinal axis of the valve component 1. For example, at least two of the main valve 2 and the auxiliary valves 3 may lie in a common plane, the common plane extending normal to the central longitudinal axis 11 of the valve component 1. Additionally or alternatively, a proximal end of one or more of the main valve 2 and the auxiliary valves 3 may be flush with a proximal end of the housing 23. Additionally or alternatively, one or more of the main valve 2 and the auxiliary valves 3 may be received in a proximally-open recess 24 at the proximal end of the housing 23. The housing 23, main valve 2, and/or the auxiliary valves 3 may pose less of an impediment to movements of instruments inserted therein due to this low-profile configuration.

FIGS. 1 and 2 illustrate an instrument access device comprising a wound retractor 30 and a valve component 1. In this case a retracting sleeve 32 has two layers and a release member 35 is provided which extends from a distal ring 31 to a proximal location external of the proximal ring assembly 8,9. A pull ring 36 is attached to the release member 35. The ring 36 is pulled to release the distal ring 31 to facilitate removal of the retractor after a procedure is concluded.

Referring to FIGS. 8 to 11 in this case the valve component 40 is a single piece and seals and rotates relative to an inner ring 41 similar to the embodiments of FIGS. 6(*a*), 6(*b*), and 7. The retractor sleeve 32 again does not rotate with the inner valve component 40. The valve component 40 may be coupled to and uncoupled from the inner ring 41. When coupled, a radial protrusion 42 on the valve component 40 may be received in a radial groove or recess 43 of the inner ring 41. Alternatively, the positioning of the protrusion 42 and the groove 43 may be reversed. Coupling and uncoupling of the valve component 40 and the inner ring 41 may have no effect on the retractor sleeve 32 since the retractor sleeve 32 is held between the inner ring 41 and the outer ring 25, and out of engagement with the valve component 40. For example, the coupling and uncoupling may not move the portion of the retractor sleeve extending between the outer ring 25 and the distal ring 31.

Referring to FIGS. 12 to 14 in this case a rotating valve component 50 has a depending leg 51 with a radial projection 52 which is engagable in a recess 53 in a ring 54. The valve component 50 is freely rotatable within the ring 54. The engagement between the projection 52 and the recess 53 facilitates locking of a proximal end of the sleeve 32 as shown in FIG. 12. The smaller valve(s) 3 rotate about the central large valve 2. The longitudinal axis of central valve 2 is the centre of rotation.

Additionally or alternatively, a disc-shaped central portion of the valve component 50 may sealingly and slidably engage, and may be rotatable relative to, an outer-ring shaped portion of the valve component 50 from which leg 51 extends distally. In this configuration, the outer ring-shaped portion of the valve component 50 may not rotate relative to the ring 54, and thus, the sleeve 32 may extend between the outer ring-shaped portion of the valve component 50 and the ring 54, and the outer ring 25 may be omitted. One or more lip seals, similar to the lip seal 20, may be provided at the juncture between the relatively rotatable components, as described above. Additionally or alternatively, it is contemplated that relatively rotatable components may have complementary engaging surfaces to provide sealing and sliding engagement between the components. For example, a protruding peripheral portion 56 of the disc-shaped central portion of the valve component 50 may be received in a groove or recess 57 in the outer-ring-shaped portion of the valve component 50.

Figure 16B:
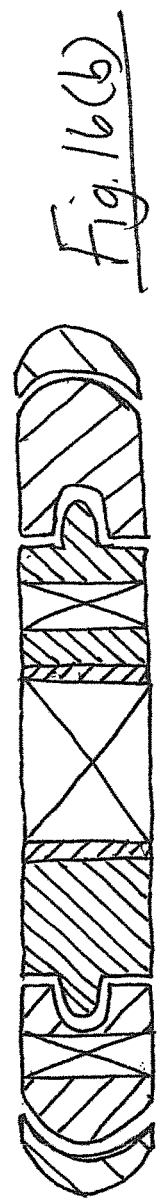
FIGS. 16(a) and 16(b) are a plan view and a schematic cross-sectional view, respectively, of another access port device.
Figure 16A:
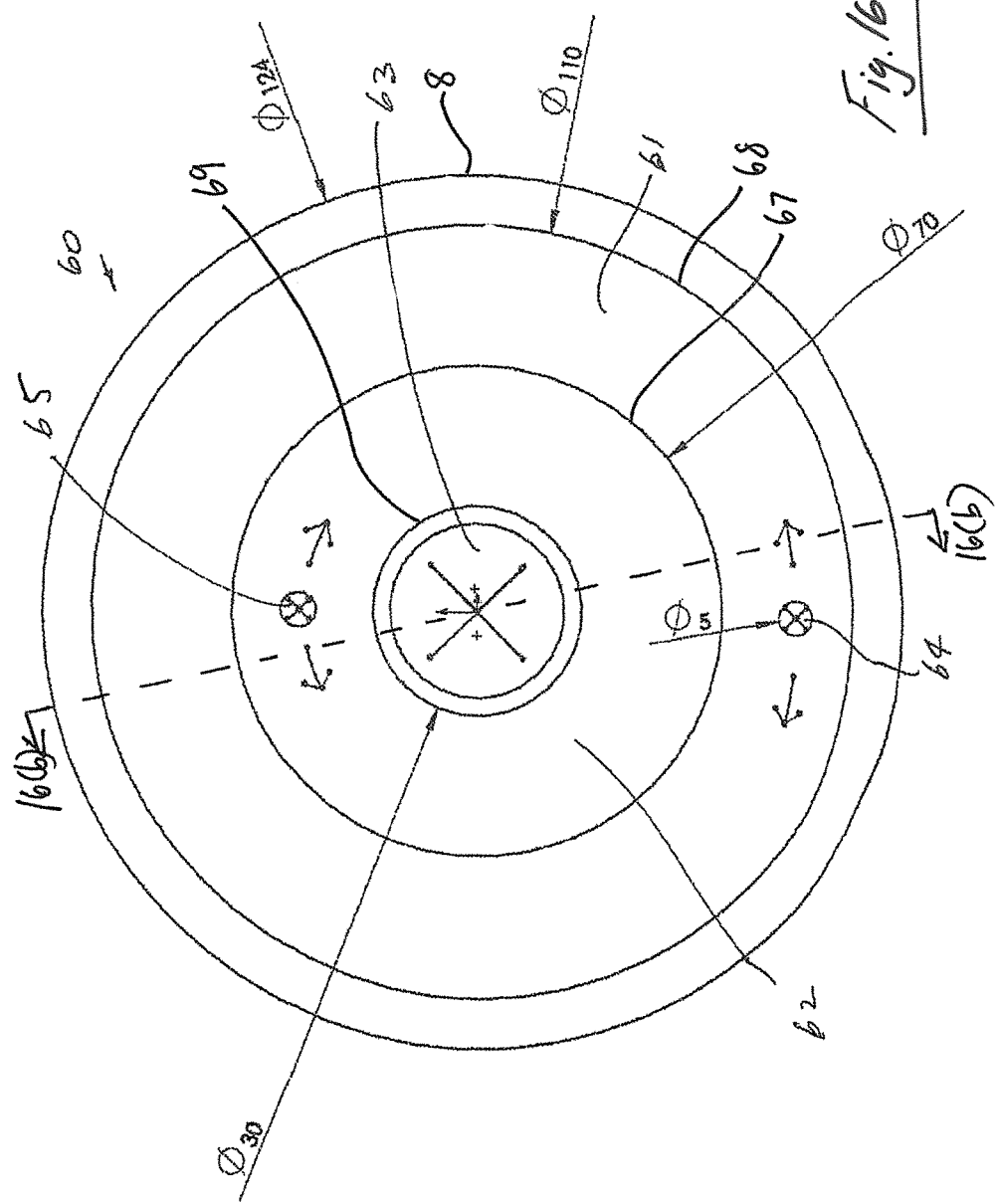
Figure 17A:
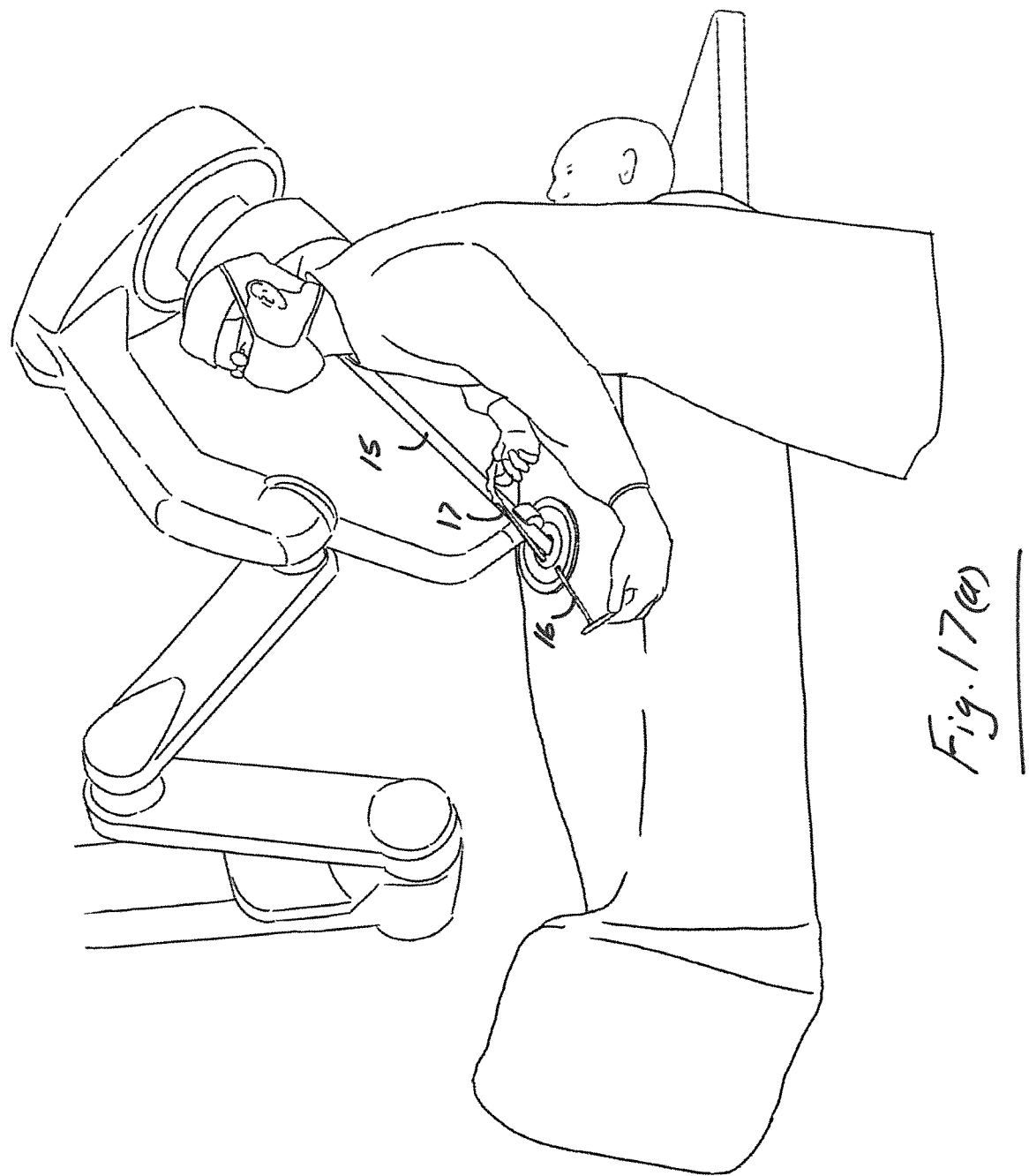
FIGS. 17(a) to 17(e) are a series of diagrams of the device of FIGS. 16(a) and 16(b) with instruments in situ.
Figure 17B:
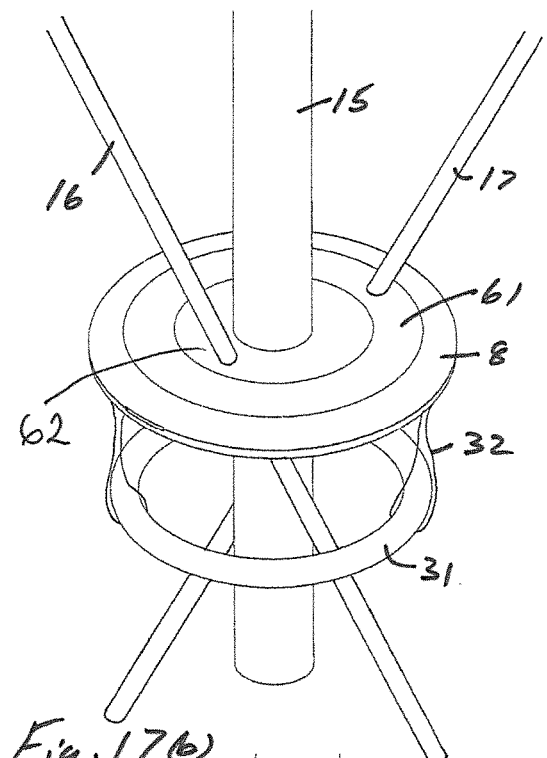
Figure 17C:
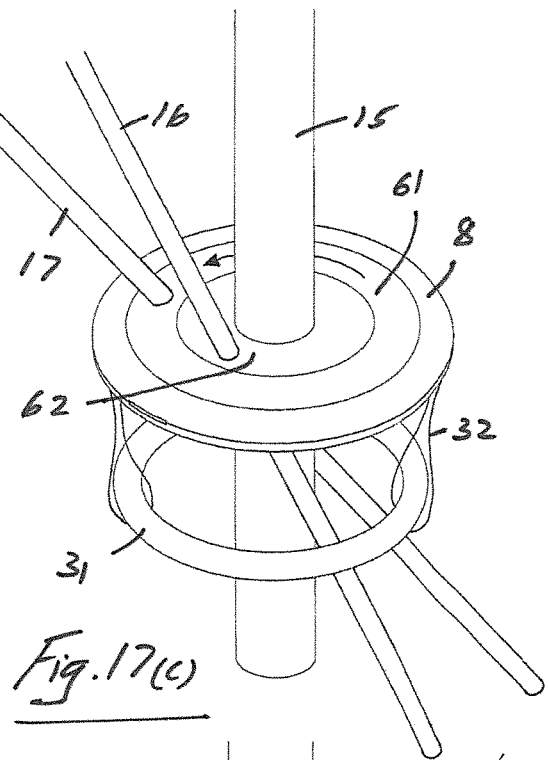
Figure 17D:
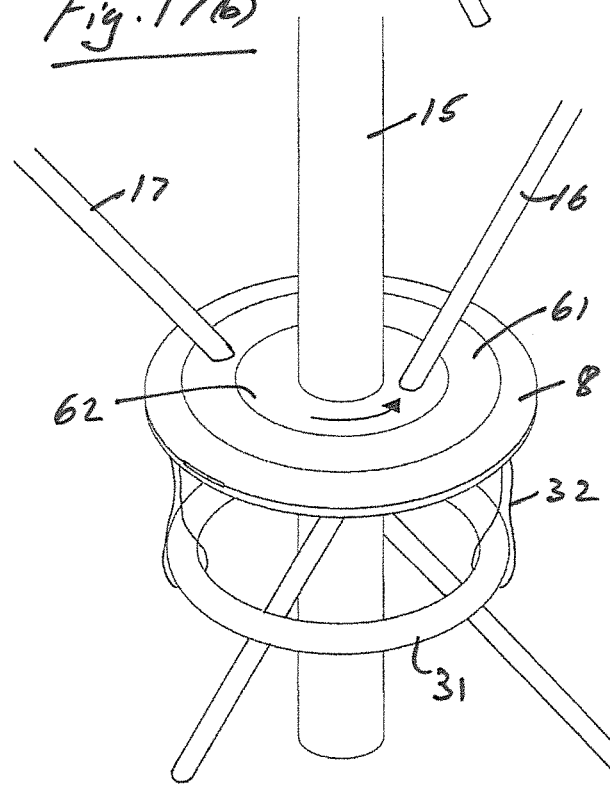
Figure 17E:
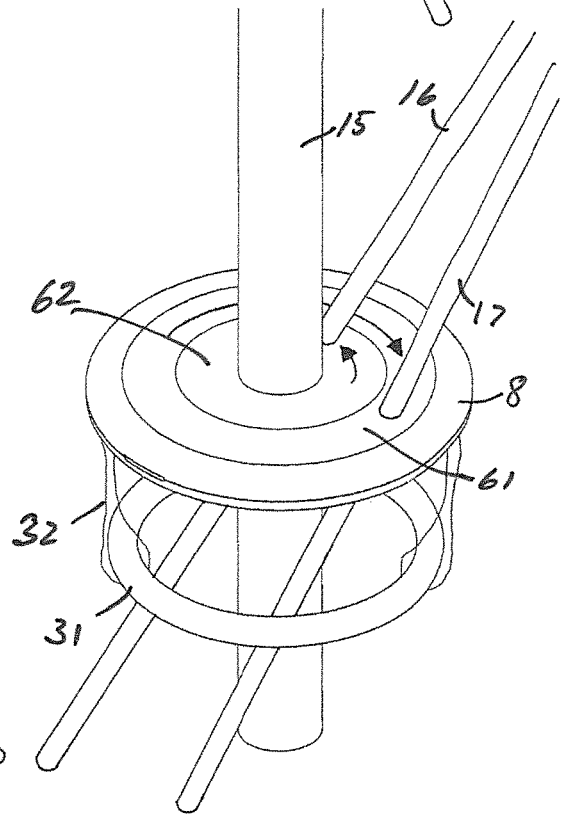

Referring to FIGS. 16(*a*), 16(*b*) and 17(*a*)-17(*e*), in one embodiment the valve component 60 has two platforms 61, 62 around the large central valve 63 to allow independent movement. Auxiliary valves 64, 65 can move independent of one another. This arrangement provides enhanced freedom of movement of the instruments 15, 16 inserted through the auxiliary valves 64, 65. The platform 62 may include an inner ring surrounding the central valve 63, the inner ring carrying one or both of the central valve 63 auxiliary valve 65. The platform 61 may include an outer ring surrounding the platform 62, the outer ring carrying the auxiliary valve 64.

One or more lip seals, similar to the lip seal 20, may be provided at the interface 67 between platforms 61 and 62, and/or at the interface 68 between the platform 61 and the proximal ring 8. It also is contemplated that the platform 61 may interface with the proximal ring 9 (FIG. 3), which may interface with the proximal ring 8, instead of the platform 61 interfacing directly with the proximal ring 8. Additionally or alternatively, relatively rotatable components may have complementary engaging surfaces (e.g., at least one protrusion for receipt in at least one groove or recess) to provide sealing and sliding engagement between the components. Surfaces of the platforms 61 and 62 may be slidingly and sealingly engaged at the interface 67, to facilitate relative rotation of the platforms 61 and 62. Surfaces of the platform 61 and the proximal ring 8 or the proximal ring 9 may slidingly and sealingly engage at the interface 68, to facilitate relative rotation of the platform 61 and the proximal rings 8 or 9.

Where the platform 1 interfaces with the proximal ring 9, the sleeve 32 may extend between the proximal rings 8 and 9. Alternatively, the sleeve may extend between the proximal ring 8 and the outer ring 25 (not shown) (FIG. 6(*a*)).

It is contemplated that the central valve 63 may be fixed (e.g., non-rotatable) relative to the platform 62, in which case the central valve 63 rotates relative to an instrument inserted therethrough when rotation is provided to the platform 62. Alternatively, it is contemplated that the central valve 63 may rotate relative to the platform 62, in which case the central valve 63 remains stationary with the instrument when rotation is provided to the platform 62. One or more lip seals, similar to the lip seal 20, and/or other engaging surfaces or structures, may be provided at the interface 69 between the central valve 63 and the platform 62, as described in previous embodiments. This may permit sealing and sliding engagement between the central valve 63 and the platform 61 at the interface, thereby facilitating relative rotation between the two. FIG. 17(*a*) illustrates a valve component of the invention in use with a central instrument 15 and accessory instruments 16, 17 in situ. In this case the central instrument 15 is controlled by a robot whilst a surgeon independently controls the movement of the accessory instruments 16, 17. Referring to FIGS. 17(*b*) and 17(*c*) it will be noted that the outer rotating ring 61 and outer rotating accessory instrument 17 rotate independently of the inner accessory instrument 16 and the inner valve platform 62. FIG. 17(*d*) illustrates that the inner rotating ring 61 and inner accessory instrument 16 rotate independently of the outer accessory instrument 17 and the central instrument 15. In this case the outer instrument 17 may remain in position. Referring to FIG. 17(*e*) in this case both the inner and outer accessory instruments 16, 17 are rotatable independent of a centrally located instrument 15. Both accessory instruments 16, 17 may be moved, but independently of one another thereby further enhancing the freedom of movement of the instruments.

Figures 18, 19:
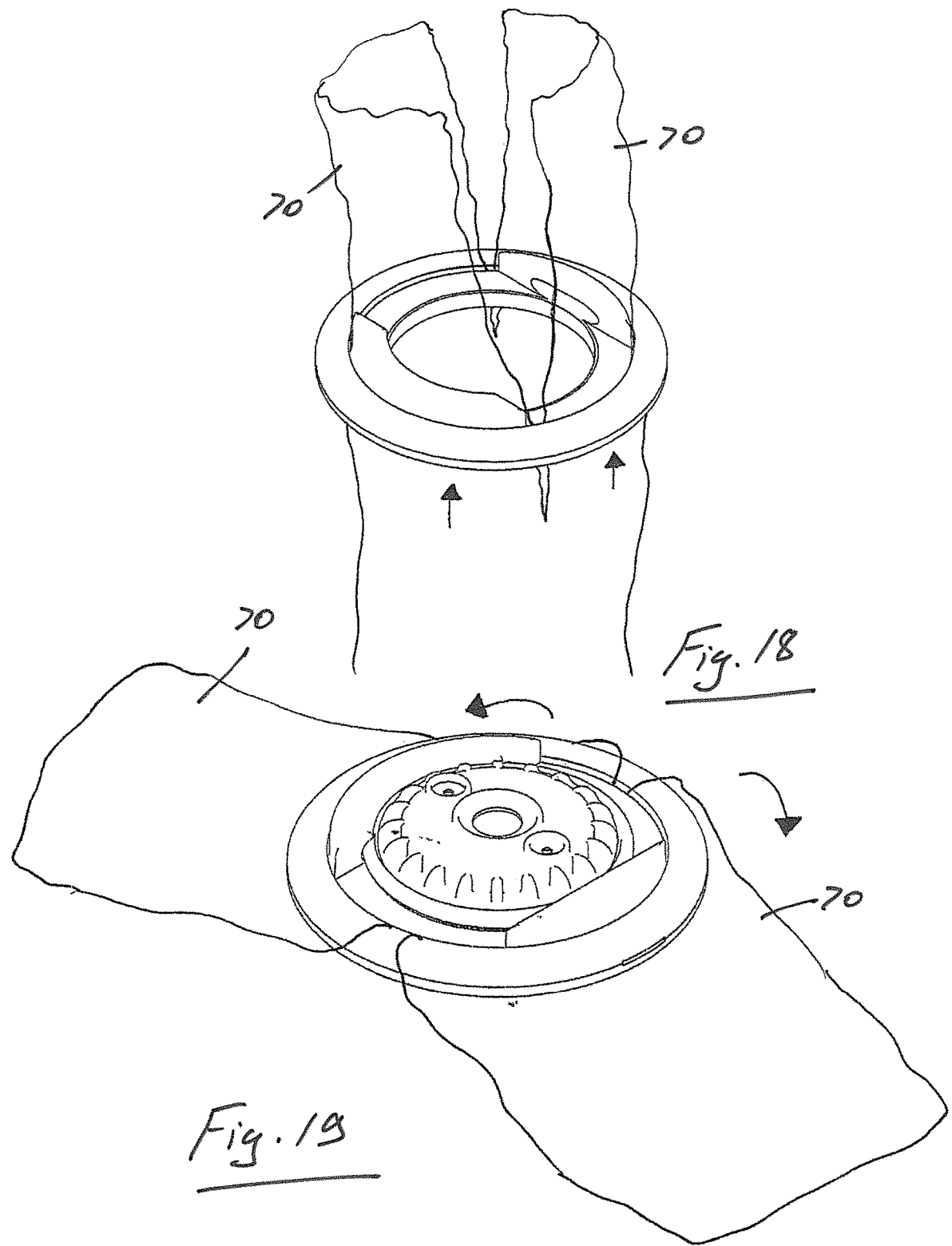
FIGS. 18 and 19 are isometric view of another access port device with a split sleeve.

Referring to FIGS. 18 and 19 there is illustrated a system in which a retracting sleeve 32 is split at the proximal end into a number of sections 70 which allows for easy removal of the sleeve from the valve space after retraction.

Figure 20:
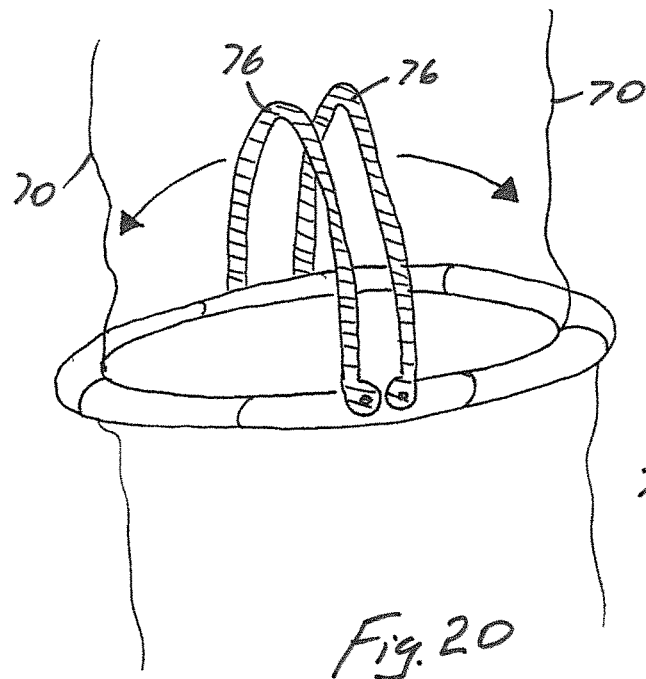
FIGS. 20 and 21 are isometric views of one clamping system for a split sleeve.
Figure 21:
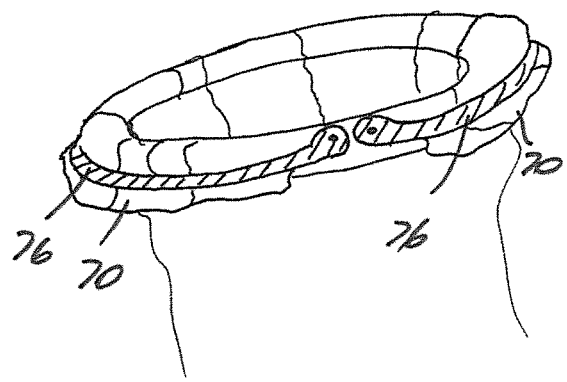
Figure 22:
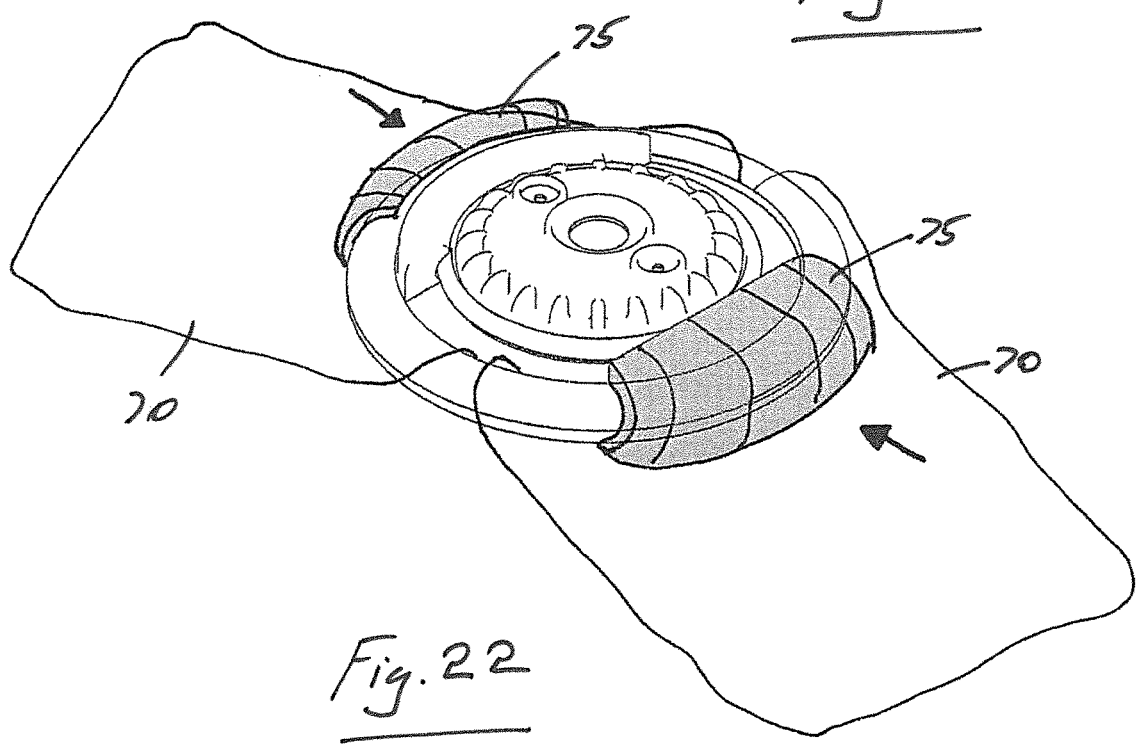
FIG. 22 is an isometric view of another clamping system for a split sleeve.

FIGS. 20 to 22 illustrate various ways to clamp/lock a split sleeve such as using separate snap-on clips 75 or integrated flap-down clamps 76.

Figure 23:
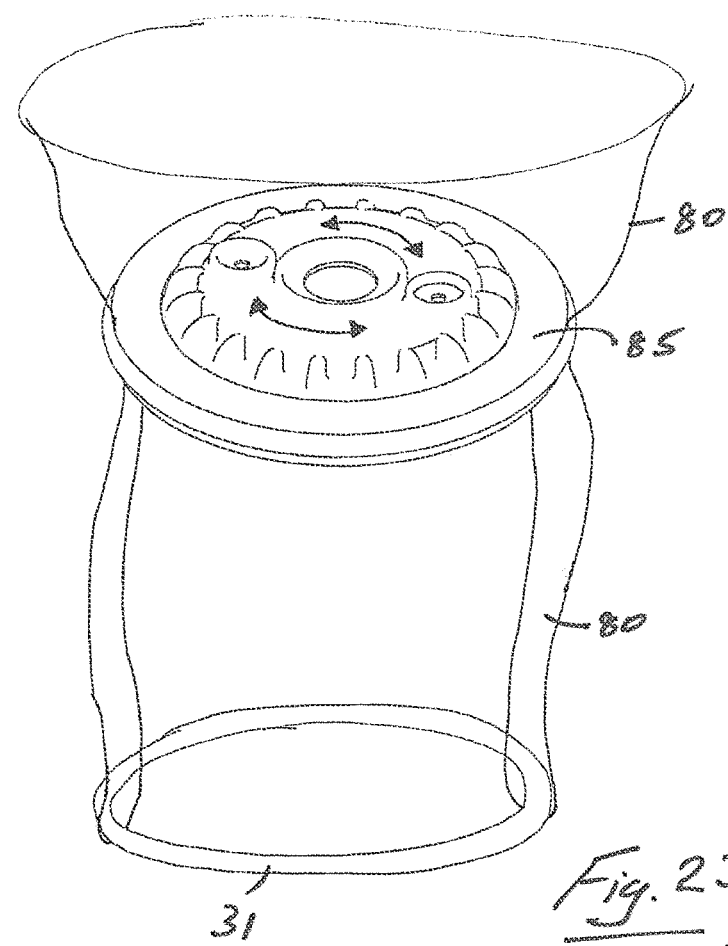
FIGS. 23 and 24 are views of another access port device with an alternative sleeve arrangement.
Figure 24:
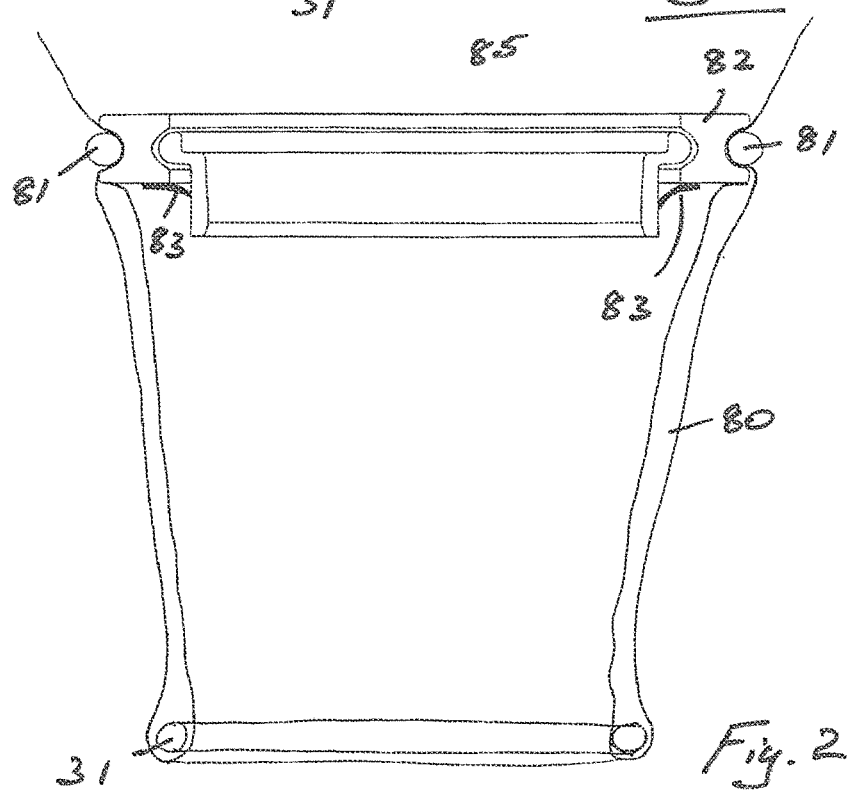

FIGS. 23 and 24 show an alternative sleeve arrangement whereby the sleeve 80 feeds externally and then through and around a rigid O-ring component 81. The internal profile is free of sleeve and a single component valve unit 85 is inserted into the outer proximal ring 82. A lip seal 83 seals the system.

FIGS. 25 and 26 illustrate flexibility in a valve system. There is a glove-like valve system 89 with a number of ports 91. The system comprises a flexible stem 90 which may, for example, be made from a thin rubber or silicone material. FIG. 26 illustrates how the valve system itself can be an extension of the retracting sleeve 32 (i.e. sleeve 32 extends proximally to provide the valve system).

FIGS. 27 to 32 illustrate various approaches to dealing with excess sleeve material. In some cases the excess sleeve material 97 following retraction is folded or bunched and this excess in the fastened to the base using a clamp 98 or clip 101 or built in secondary ring 100. The arrows illustrate the inherent flexibility of the valve component.

In some cases at least some of the valves 2, 3 may be mounted on a stalk which is laterally flexible and longitudinally rigid to enhance the freedom of movement of an instrument.

Figure 34:
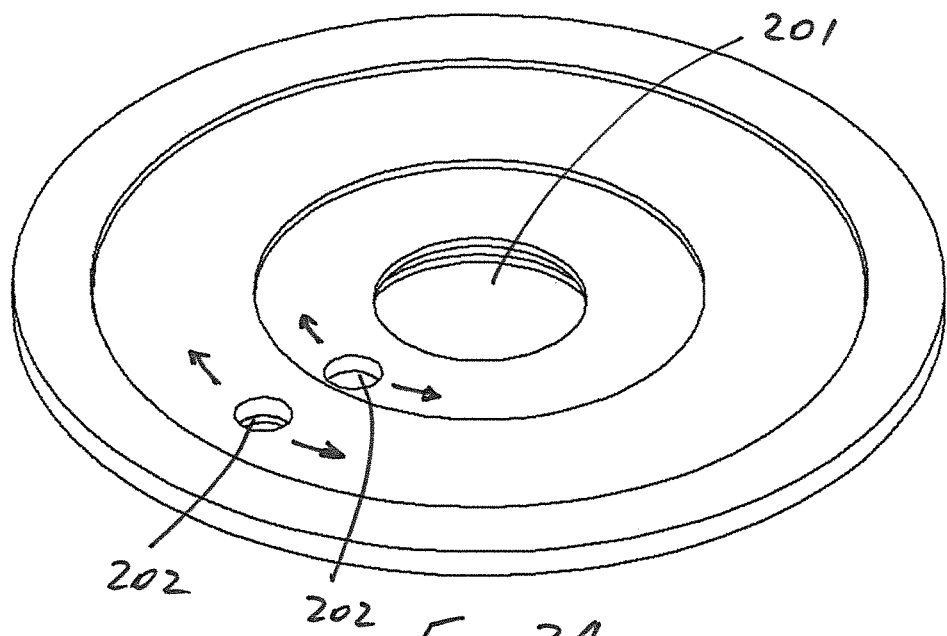
FIG. 34 is a perspective view of one access port.
Figure 35:
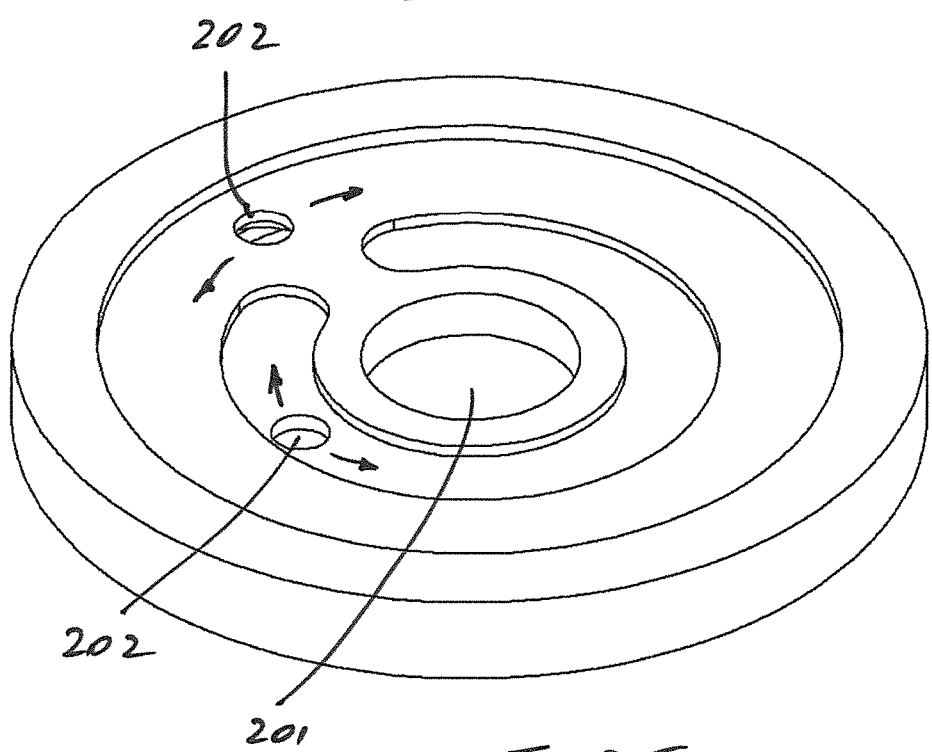
FIG. 35 is a perspective view of another access port.

Referring to FIGS. 33(a) to 33(h) there are illustrated various configurations of assistant ports around a central port 201. FIG. 33(a) illustrates a single assistant port 202 which is fully rotatable around the central port 201. FIG. 33(b) shows a single assistant port 202 which can rotate in an arc through any range of angles, for example, up to 300°. The advantage of the arrangement of FIG. 33(b) is that the port is more robust as there is additional material in the region 203. FIG. 33(c) to (e) illustrate various sectors within which assistant ports 202 can be moved in the same orbit. In FIGS. 33(f) to (h) the assistant ports 202 can move in different orbits for enhanced flexibility of movement. FIGS. 34 and 35 are perspective views of access ports with central ports and rotatable auxiliary ports 202. In one example in which assistant ports may move in different orbits, each of the assistant ports 202 may be on its own platform, and the platforms may be slidably and sealingly engaged to allow one platform to rotate relative to the other (FIGS. 16(a), 16(b), and 17(a) to 17(e)).

Referring to FIGS. 33(i) and (j) in addition to or as an alternative to rotation, various assistance ports 205 may be arranged around a central port 206 and an assistant port desired for a particular procedure can be readily selected depending on, for example, the access angle required. The assistance ports in these configurations can be provided with an extended neck or domed flexible leg to facilitate movement.

Figure 36:
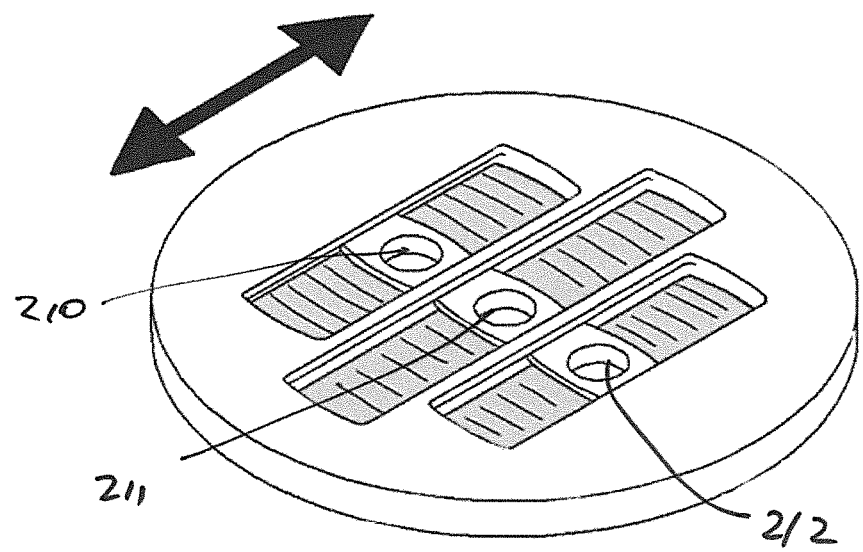
FIGS. 36 and 37 are isometric and plan views illustrating one form of sealing in an access port.
Figure 37:
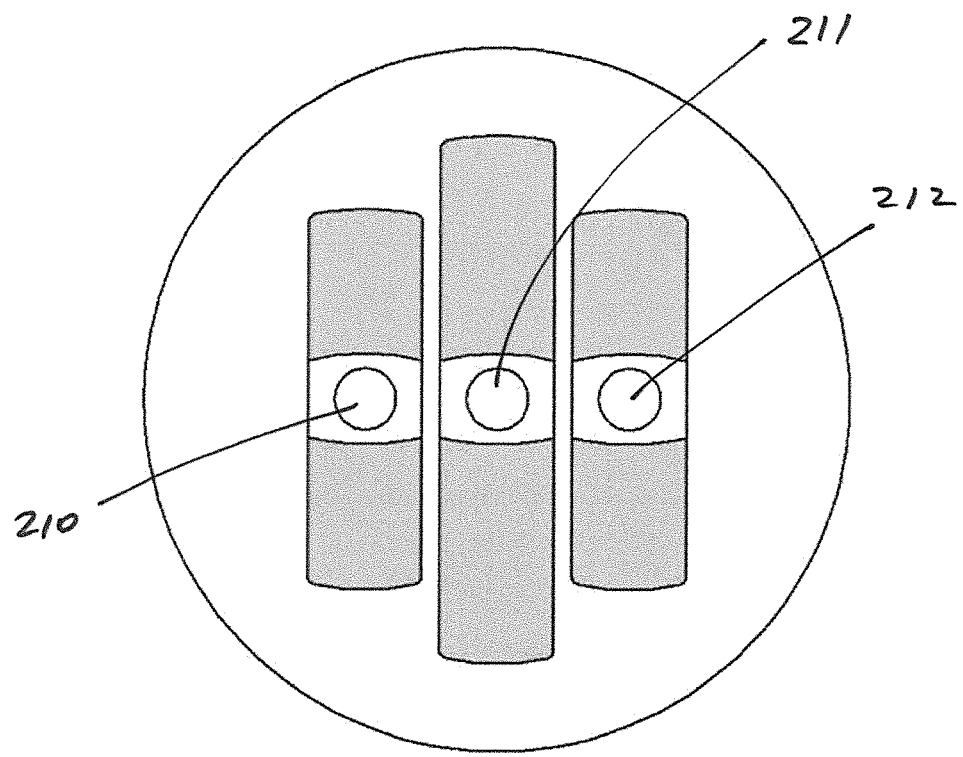

Movement of the ports can be facilitated whilst maintaining a seal between the moving ports in a number of different ways. For example, referring to FIGS. 36 and 37 ports 210, 211, 212 can be provided in flexible strips of a sealing material which can be compressed or stretched as the ports 210, 211, 212 are moved whilst maintaining a seal.

Figure 38:
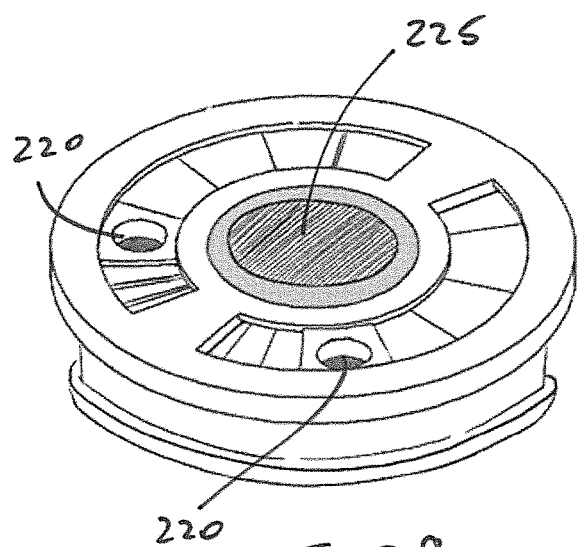
FIGS. 38 and 39 are isometric and plan views illustrating another form of sealing.
Figure 39:
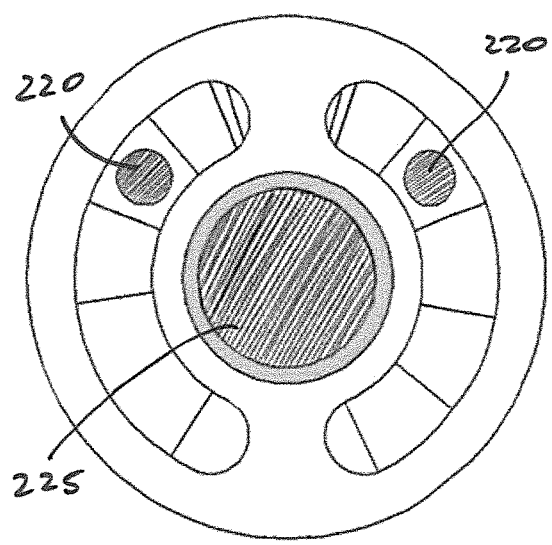
Figure 40:
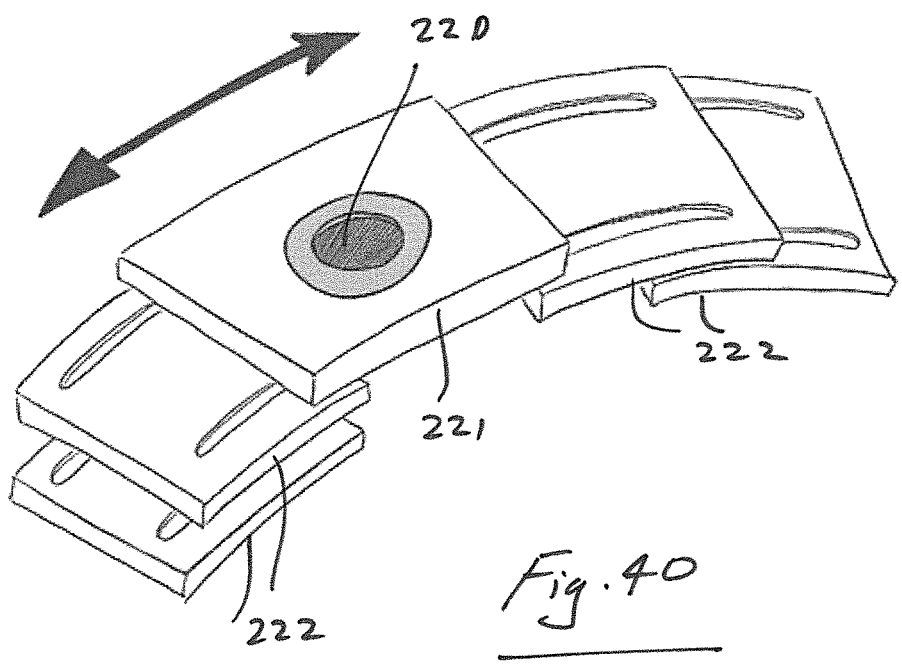
FIG. 40 is a perspective enlarged view illustrating one form of sealing.

Referring to FIGS. 38 to 40, a port 220 may be provided on a sealing element such as a tile 221 and there may be a plurality of tiles 222 which overlap to maintain a seal as the port 220 is moved relative to a central port 225.

Figure 41:
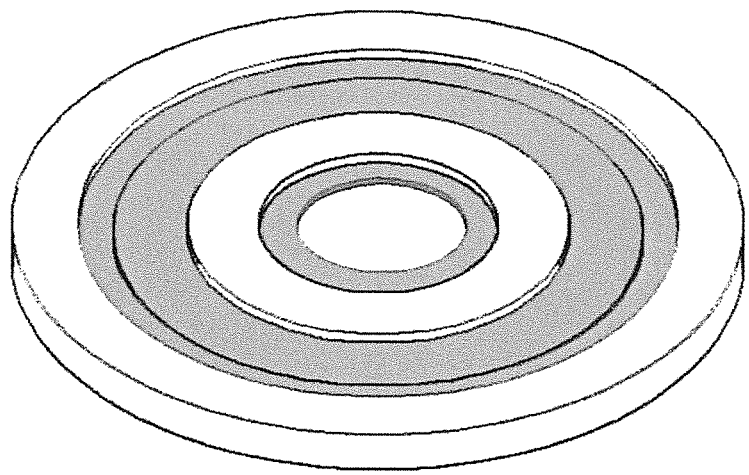
FIGS. 41 and 42 illustrate further access ports according to the invention.

Referring to FIG. 41 there may be two discs 231, 232 of a sealing material such as a gel that overlap. Internal positive pressure maintains a seal. A floating disc slides along the overlap sealing any leaks caused by an instrument passing through the overlap.

Figure 42:
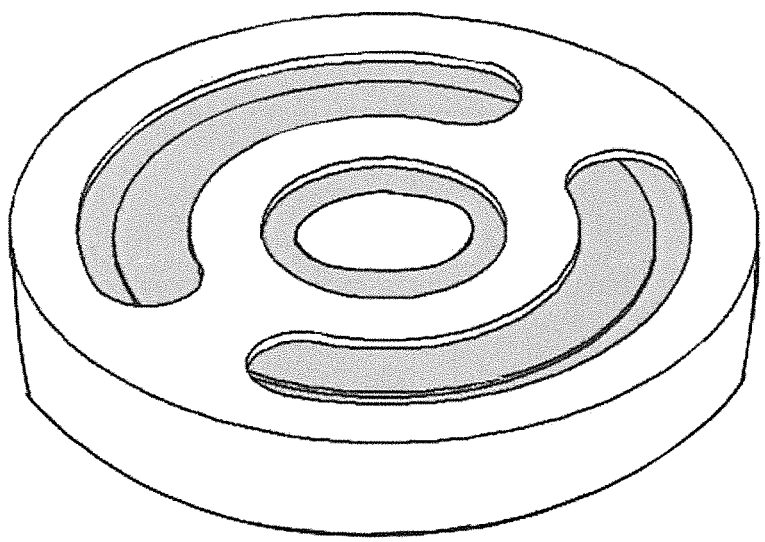
Figure 43:
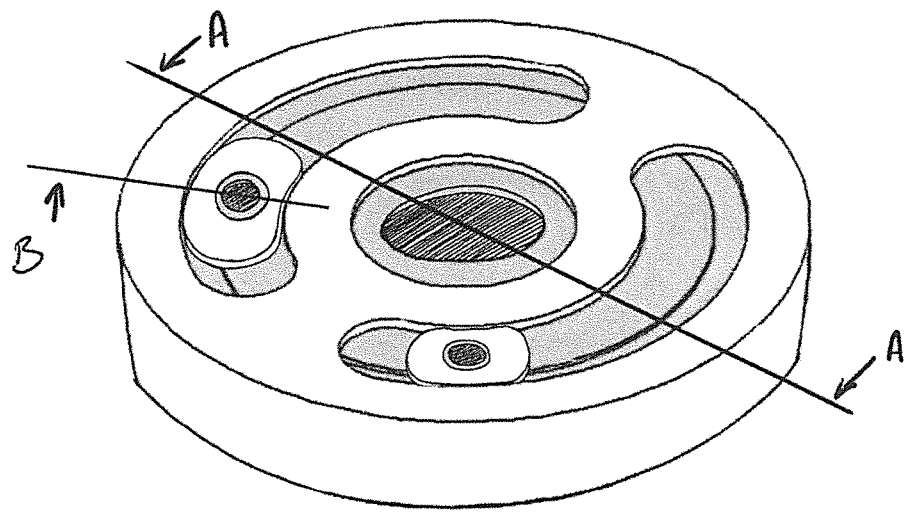
FIG. 43 is a view of an access port with accessory instruments in situ.
Figure 44:
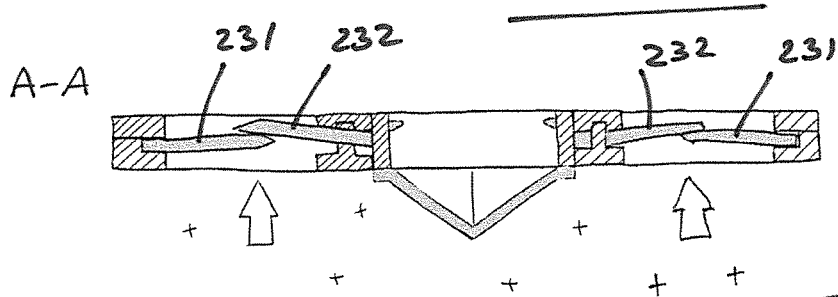
FIG. 44 is a cross sectional view on the line A-A in FIG. 43.
Figure 45:
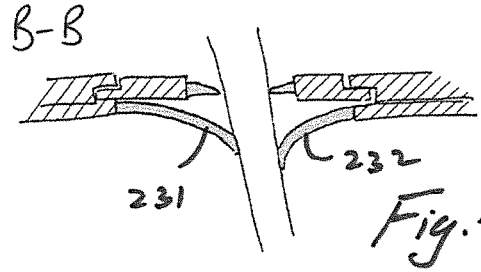
FIG. 45 is a cross sectional view on the line B-B in FIG. 43.

The arrangement of FIG. 41 facilitates full 360° rotation whilst in the device of FIGS. 42 and 43 the assistant ports are confined to move through an arc.

Figure 46:
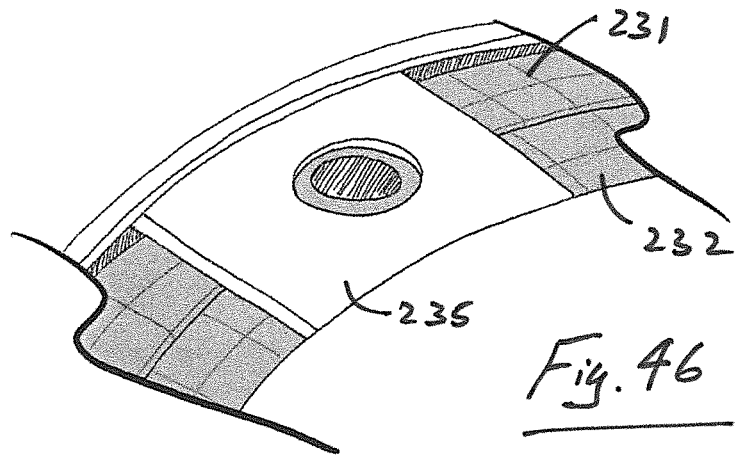
FIG. 46 is an enlarged perspective view of a floating plate seal.

FIG. 46 illustrates a floating plate 235 that seals around an instrument and over the gap created by an instrument in the overlapping seals 231, 232. The plate 235 provides a cap over the split seal.

FIG. 47 illustrates as access port which comprises a central port 300 and an assistant port 301. A tear drop shaped cap/plate 304 rotates with the assistant port 304 as an instrument travels through a split seal 305. The cap 304 seals around an instrument inserted into the assistant port 301 and provides a sealing cap over the portion of the split type seal 305 that is displaced by the assistant instrument.

FIG. 48 illustrates an access port in which one assistant port 238 is fixed with respect to a central port 239. A smaller assistant port 240 is provided and both ports can move independently of one another.

FIGS. 49 and 50 illustrate another access device in which assistance ports 241, 242 are arranged around a central port 243 and a flexible membrane 245 is provided between the ports 241, 242. The membrane 245 facilitates movement between the ports 241, 242 whilst maintaining sealing.

Referring to FIG. 51 there is illustrated another access port comprising a central port 320 and a sealed slot 321 through which an assistant instrument may be inserted at any desired angle around the central port 320. The slot 321 is covered by a plurality of petal-shaped cap members 322 that are individually pivotable about pivot points 323. The petals 322 rotate about the pivots 323 out of the way of an assistant instrument as it passes through the slot 321. The petal shaped caps minimise gas release when an assistant instrument is inserted without restricting the location or movement of the assistant instrument.

Figure 52:
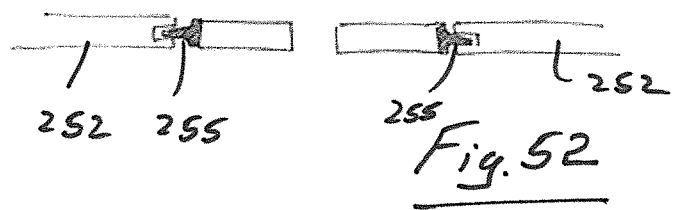
FIGS. 52 to 58 illustrate various sealing systems between rotatable parts of access ports of the invention.
Figure 53:
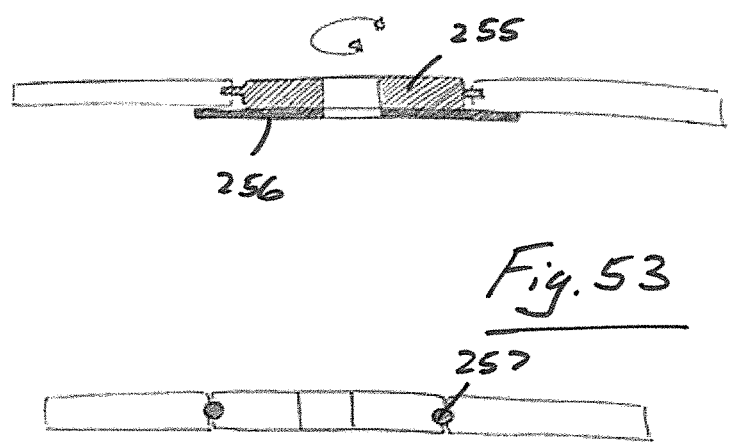
Figure 54:
Figure 55:
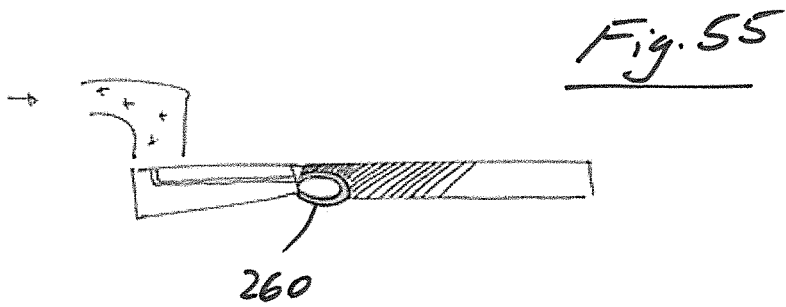

FIGS. 52 to 58 illustrate various sealing systems between the access port elements 251, 252 that rotate relative to one another. A seal 255 may be retained by a male/female type engagement as illustrated in FIG. 52. An additional internal flexible sealing strip 256 may be provided (FIG. 53). Another alternative is an O-ring type seal 257 (FIG. 54) or a skirt type seal 258 (FIG. 55).

Figure 56:

In some cases the seal may be expandable, for example by inflation, in one case using a supply of insufflation gas which would usually be provided to the access port. One such inflatable seal 260 is shown in FIG. 56.

Figure 57:
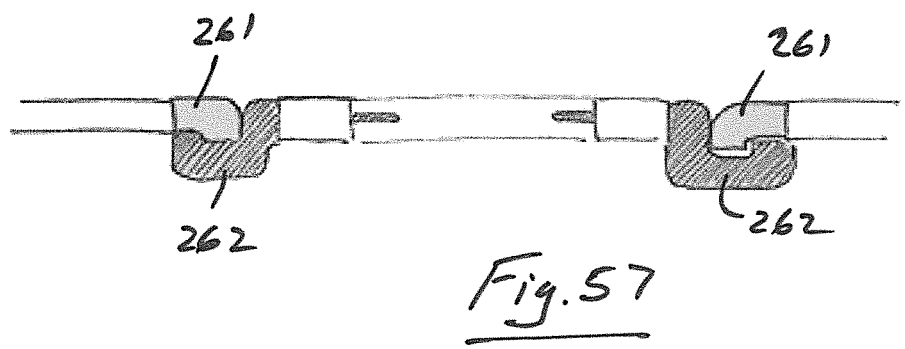

There may also be overlapping/interengagable seals 261, 262 as shown in FIG. 57.

Figure 58:
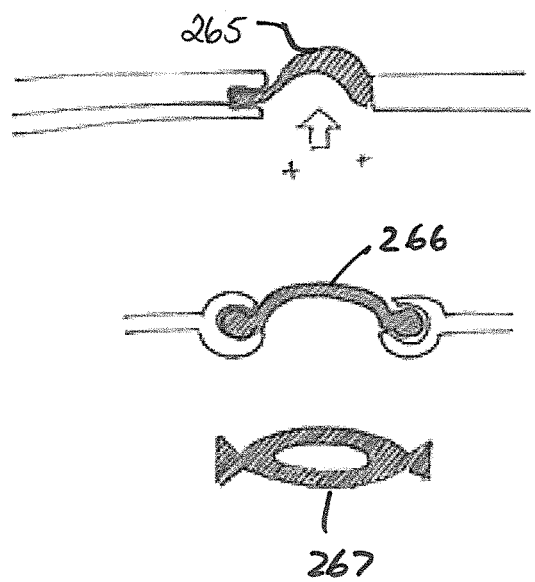
Figure 59:
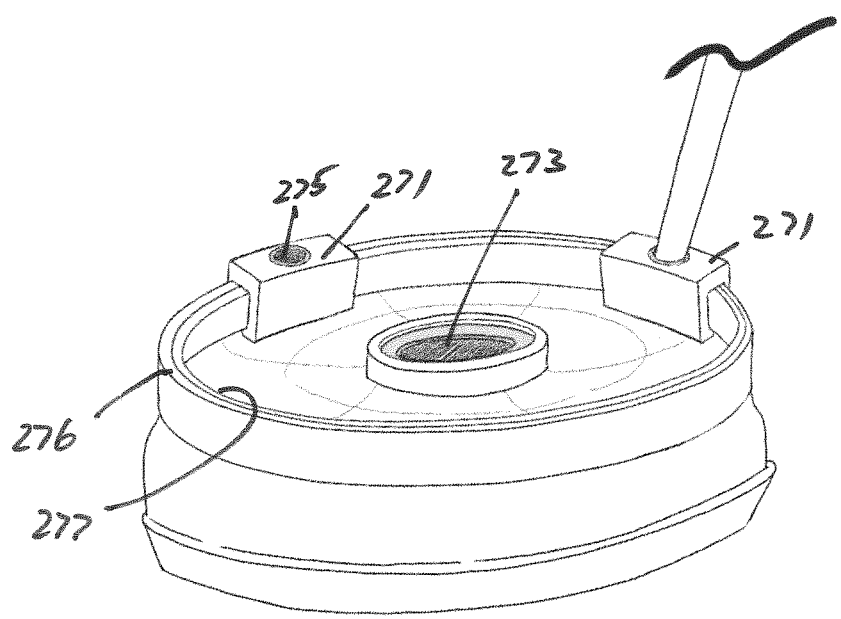
FIGS. 59 to 62 are a series of images of another sealing system.
Figure 60:
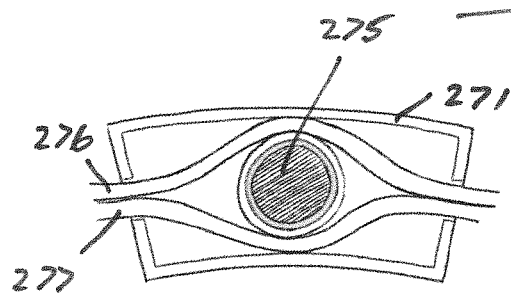
Figure 61:
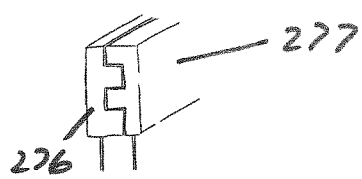

The seals may have any desired profile such as the profiles 265, 266, 267 illustrated in FIG. 58. The profile may be such that the seal is pushed outward under internal pressure. Insufflation pressure on one side may also assist in pushing the seal against its opposite surface.

FIGS. 59 to 62 illustrate another access device 270 having a central port 273 in which an assistant port 275 is provided in a block 271 which is rotatable around the outer periphery to close interengagable elements 276, 277 somewhat in the manner of the plastic bag closing system referred to as zip-loc. The assistant port 275 includes a valve 274. Such a system ensures that a seal is maintained whilst facilitating movement of the assistant ports.

Figure 62:
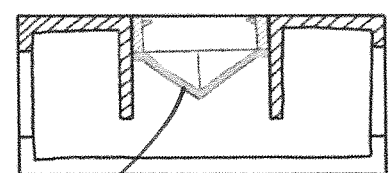
Figure 63:
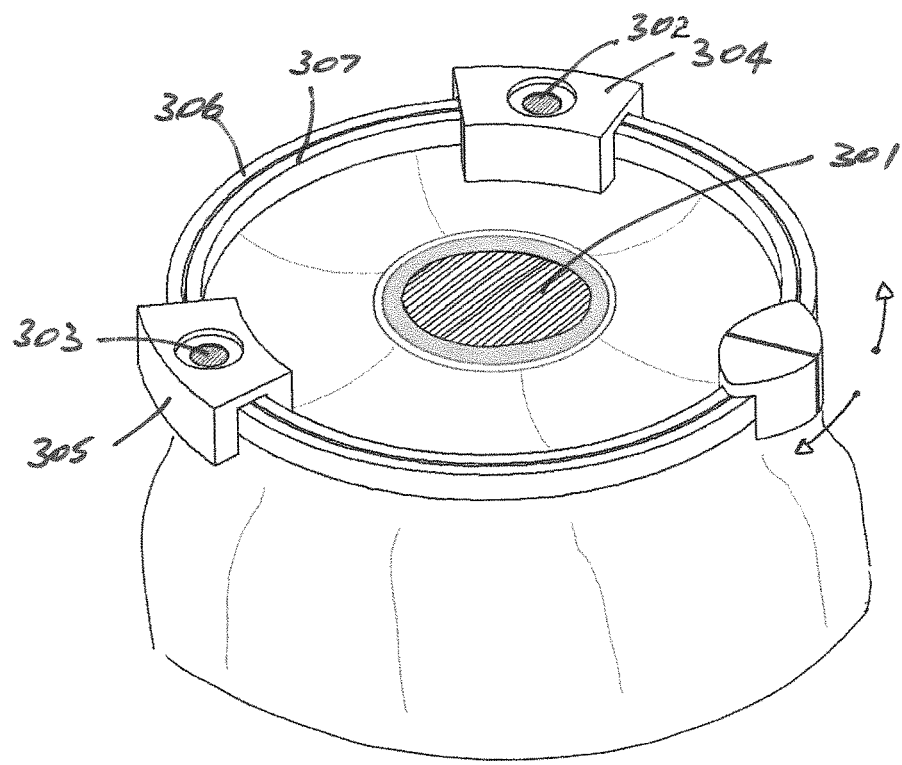
FIGS. 63 to 66 are a series of images of another access port according to the invention.

Referring to FIGS. 63 to 66 there is illustrated another access device 300 according to the invention. The access device 300 comprises a central port 301 and two assistant ports 302, 303. The assistant ports 302, 303 are similar to the assistant ports described with reference to FIGS. 59 to 62. The assistant ports 302, 303 are provided in blocks 304, 305 which are rotatable around the outer periphery to close interengagable closure elements 306, 307 somewhat in the manner of a zip-lock type closure mechanism. In this case, the central port 301 comprises a valve 310 which is coupled, in this case, by means of a membrane 311 to the closure element 307. The access port in this case has a mechanism for opening the port while in situ, for example, for removal of a large tissue sample. The opening mechanism comprises two sliders 320, 321 which are rotatably mounted to closure elements 306, 307 and are moved in opposite directions as illustrated in FIG. 63 to open the zip-lock closure.

Figure 67:
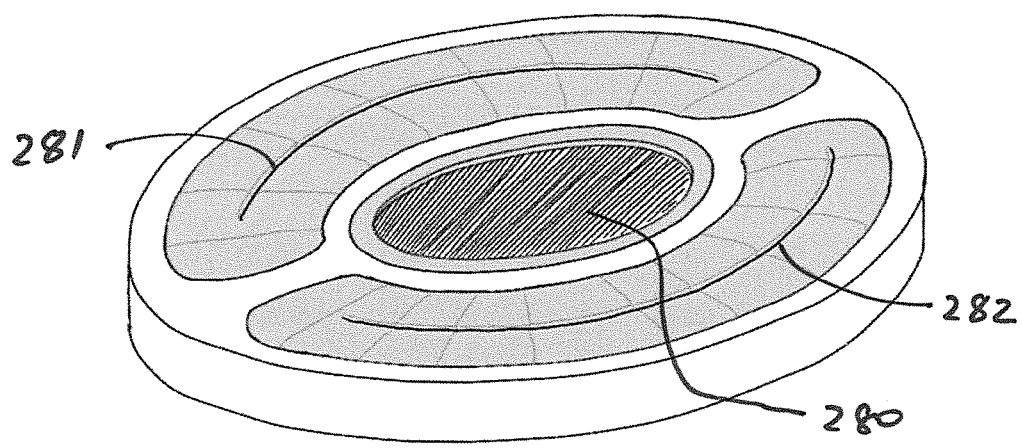
FIGS. 67 to 69 are views of another access port according to the invention.
Figure 68:
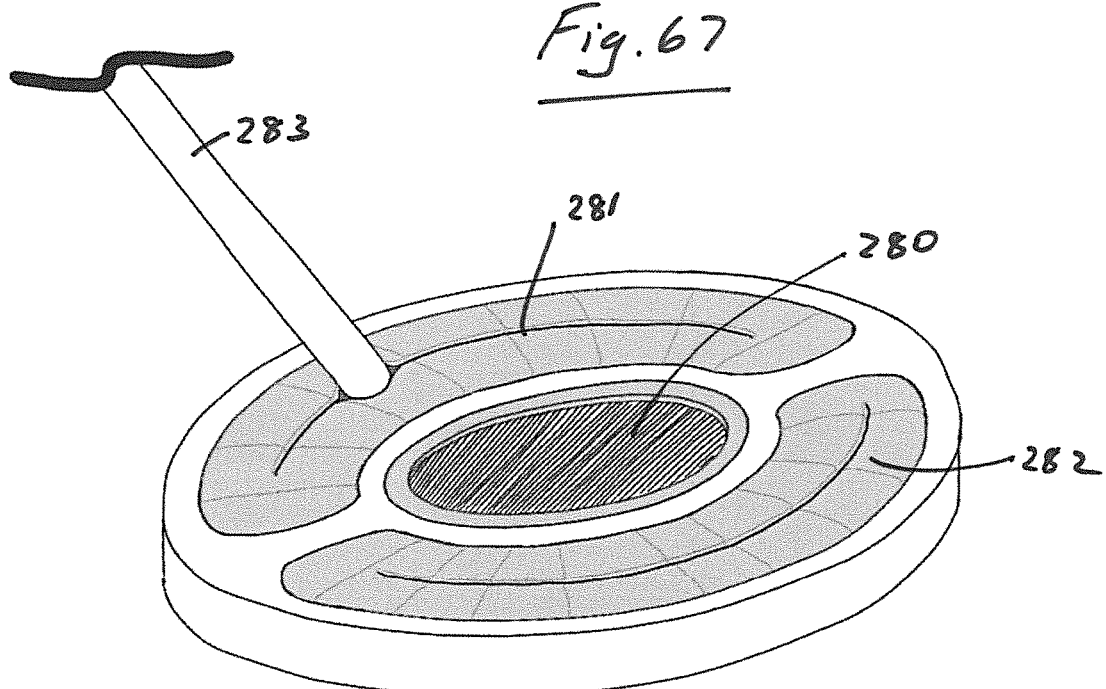
Figure 69:
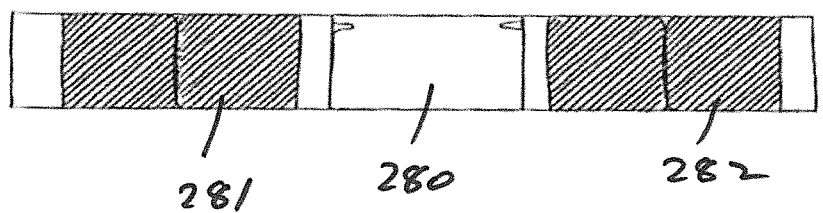

Referring to FIGS. 67 to 69 there is illustrated another access device which again comprises a central port 280 and in this case two regions 281, 282 into which an assistant instrument 283 can be inserted and rotated around the central port 280. The regions 281, 282 have a sealing material such as a self sealing gel material through which an instrument can be readily inserted and rotated around the central port 280.

Figure 64:
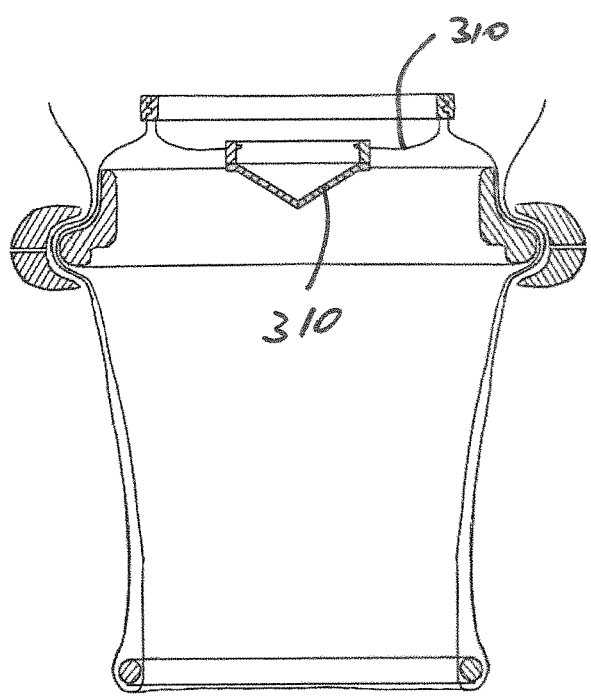
Figure 65:
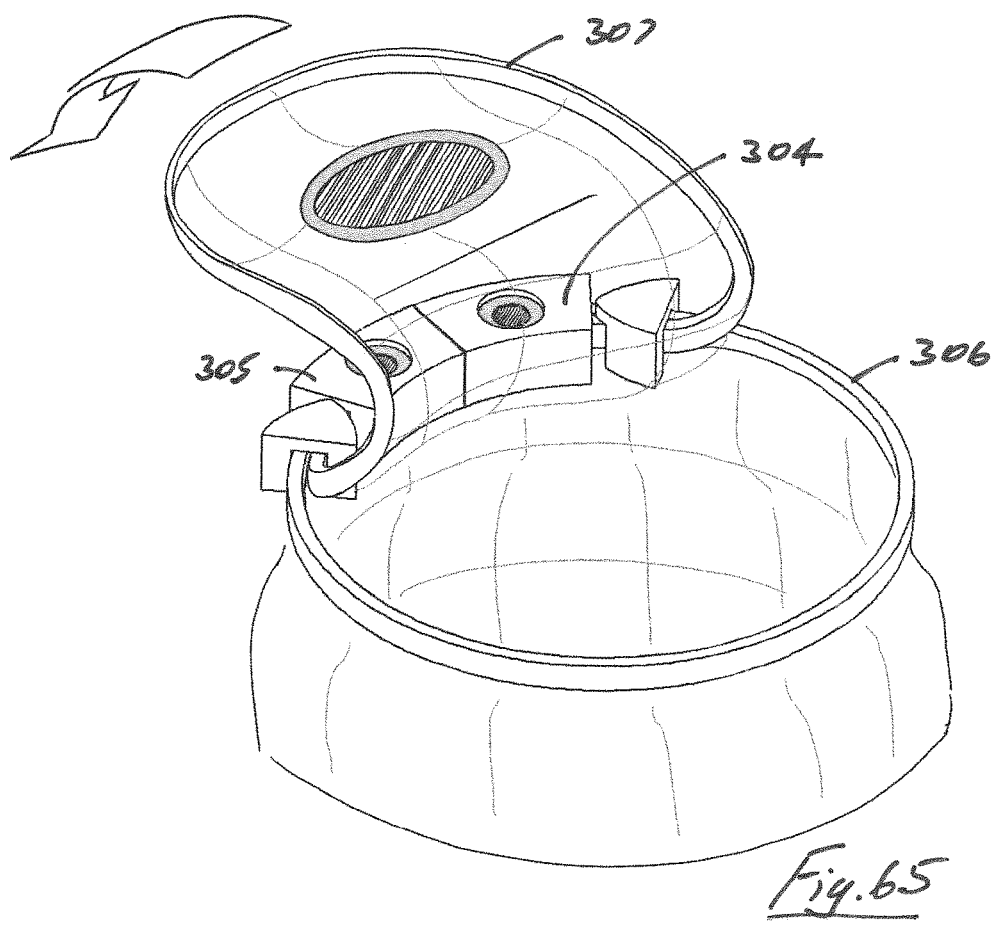
Figure 66:
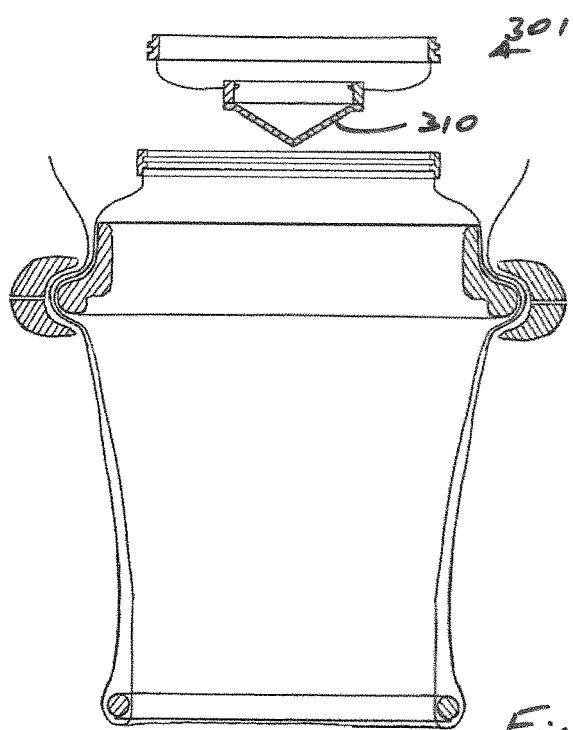
Figure 70:
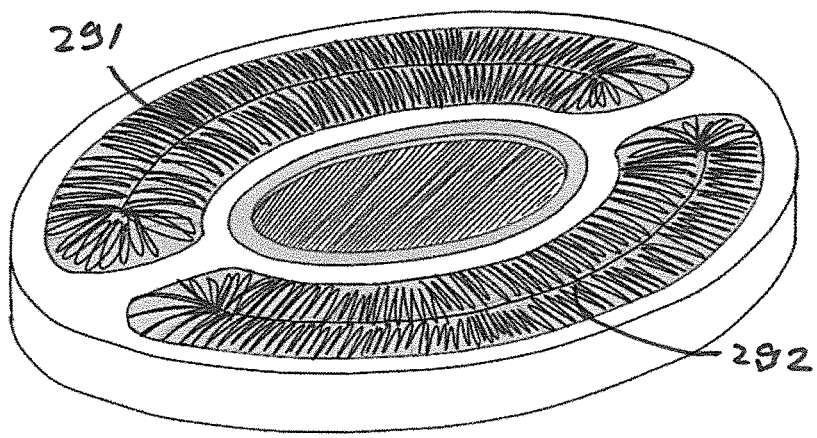
FIGS. 70 to 72 are views of a further access port according to the invention.
Figure 71:
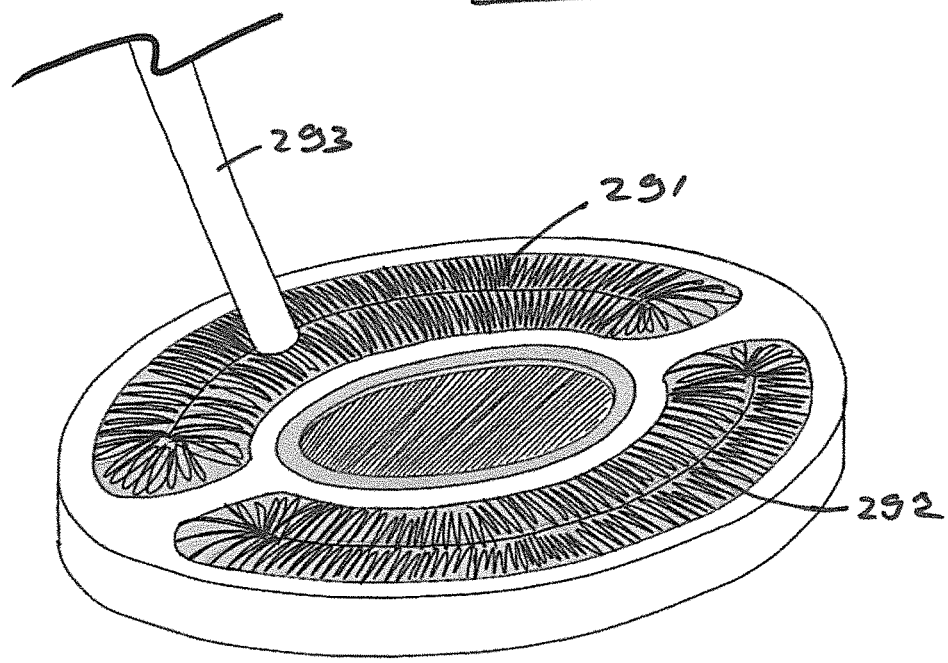
Figure 72:
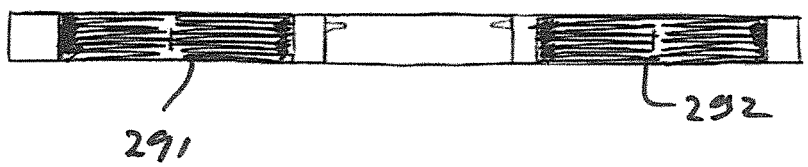

FIGS. 70 to 72 illustrate another access port which is similar to that of FIGS. 62 to 64 except that in this case a fibrous type sealing material 291, 292 is provided for sealing engagement with an assistant instrument 293.

The access ports of the invention are useful when used in surgery which involves robots. Such robotic instruments are inserted through the central access port and at least one assistant port is movable relative to the central port. This ensures that a surgeon can use the assistant ports to open up the operating field so that the robotic instruments can be used effectively and efficiently. The assistant port can be moved through a range of positions, depending on the instruments inserted and/or the operative field required. For example, instruments inserted through one or more assistant ports can readily move viscera to optimise vision and to ensure that the use of robotically operated instruments is optimised.

The invention is not limited to the embodiments hereinbefore described, with reference to the accompanying drawings, which may be varied in construction and detail.

The invention claimed is:

1. An instrument access device for use in robotic surgery, comprising:
    a base including an outer ring and a retraction portion; and
    a valve component mounted to the base, wherein a proximal portion of the retraction portion is positioned between the outer ring of the base and the valve component to maintain a position of the proximal portion relative to the base,
    wherein the valve component includes
        a robot-instrument-receiving valve, the robot-instrument-receiving valve having a central axis; and
        at least one auxiliary valve, the at least one auxiliary valve having a central axis,
        wherein the central axis of the at least one auxiliary valve is located radially outwardly of the central axis of the robot-instrument-receiving valve, and wherein a size of the robot-instrument-receiving valve is larger than a size of the at least one auxiliary valve.

2. An instrument access device as claimed in claim 1, further comprising a seal between the valve component and the base, wherein the base comprises a portion of an access port.

3. An instrument access device as claimed in claim 2, wherein the access port includes:
    a longitudinal axis;
    a proximal ring-shaped portion for location externally of an opening in a body; and
    a distal ring-shaped portion for location within the opening in the body,
    wherein the retraction portion extends proximally from the distal ring-shaped portion and laterally movable with respect to the proximal ring-shaped portion.

4. An instrument access device as claimed in claim 3, wherein the base includes the proximal ring-shaped portion of the access port and the valve component is rotatably mounted to the proximal ring-shaped portion, and wherein the proximal ring-shaped portion comprises an outer proximal ring and an inner proximal ring.

5. An instrument access device as claimed in claim 4, wherein the valve component is rotatably mounted to the inner proximal ring.

6. An instrument access device as claimed in claim 2, wherein the valve component includes one of a radial protrusion or a radial groove sized to mate with one of a radial protrusion or a radial groove of the base, the mating connection allowing for coupling, uncoupling, and rotation of the valve component relative to the base.

7. An instrument access device as claimed in claim 1, wherein the size of the robot-instrument-receiving valve is at least five times greater than the size of the at least one auxiliary valve.

8. An instrument access device as claimed in claim 1, wherein the valve component comprises at least two auxiliary valves.

9. An instrument access device as claimed in claim 8, wherein a first valve from the at least two auxiliary valves is positioned closer to the central axis of the robot-instrument-receiving valve than a second valve from the at least two auxiliary valves.

10. The instrument access device of claim 1, wherein at least a portion of a robotically-controlled instrument is configured to be positioned within the robot-instrument-receiving valve.

11. The instrument access device of claim 10, wherein at least a portion of at least one manually-controlled instrument is configured to be positioned within one of the at least one auxiliary valves.

12. An instrument access device comprising:
    a central robot access port; and
    at least one auxiliary access port which is offset from the central robot access port and configured to receive a robotically-controlled instrument extending at least partially through the central robot access port,
    wherein a size of the central robot access port is at least approximately five times greater than a size of the at least one auxiliary port.

13. An instrument access device as claimed in claim 12, further comprising a plurality of auxiliary access ports which are spaced-apart around the central robot access port, wherein at least one of the auxiliary access ports is rotatable with respect to the central robot access port.

14. An instrument access device as claimed in claim 13, wherein each rotatable auxiliary port is rotatable through an angle of at least 60°, at least 90°, at least 120°, at least 150°, at least 180°, at least 210°, at least 240°, at least 270°, at least 300°, at least 330°, with respect to the central robot access port.

15. A method of providing access to a patient for robotic surgery using an instrument access device comprising:
    an access port including:
        a longitudinal axis;
        a proximal base for location externally of an opening in a body;
        a distal ring for location within the opening in the body;
        a retraction sleeve extending between the proximal base and the distal ring; and
    a valve component configured to receive a robotically controlled instrument, the valve component rotatably coupled to the proximal base and having a center line collinear with the longitudinal axis of the access port, the valve component including:
        a robot-instrument-receiving main valve centered about the center line of the valve component, and
        a plurality of manual-instrument-receiving accessory valves each located radially outwardly of the robot-instrument-receiving main valve and rotatable around the robot-instrument-receiving main valve, wherein a size of the robot-instrument-receiving main valve is larger than a size of the each of the plurality of manual-instrument-receiving accessory valves, wherein the method comprises:
    positioning the instrument access device in an opening in a patient's body;

inserting a robot instrument in the robot-instrument-receiving main valve; and
inserting a manual instrument in at least one manual-instrument-receiving accessory valve from the plurality of manual-instrument-receiving valves.

16. The method of claim 15, wherein a distance of a first manual-instrument-receiving accessory valve from the plurality of manual-instrument-receiving accessory valves to the center line of the valve component is greater than a distance of a second manual-instrument-receiving accessory valve from the plurality of manual-instrument-receiving accessory valves to the center line of the valve component.

17. The method of claim 15, wherein the proximal base includes an inner ring and an outer ring, the method further comprising:
positioning the inner ring between the outer ring and the valve component; and
fixing the inner ring with respect to the outer ring, wherein the valve component is rotatably coupled to the inner ring.

18. An instrument access device comprising:
an access port including a proximal base for location externally of an opening in a body; and
a valve component rotatably coupled to the proximal base, the valve component including:
one of a radial protrusion or a radial groove sized to mate with one of a radial protrusion or a radial groove of the proximal base, the mating connection allowing for coupling, uncoupling, and rotation of the valve component relative to the proximal base;
a first valve centered about a center line of the valve component, the first valve having a diameter of at least approximately 25 mm; and
at least one second valve located radially outwardly of the first valve, the at least one second valve having a diameter less than the diameter of the first valve,
wherein the instrument access device is configured to receive at least a portion of a robotically-controlled instrument within the first valve.

19. An instrument access device as claimed in claim 18, wherein the at least one second valve is rotatable with respect to the first valve.

20. The instrument access device of claim 18, wherein at least one of the second valves has a diameter of 5 mm.

* * * * *